United States Patent [19]

Bös

[11] Patent Number: 5,494,928
[45] Date of Patent: Feb. 27, 1996

[54] INDOLE DERIVATIVES

[75] Inventor: Michael Bös, Rheinfelden, Switzerland

[73] Assignee: Hoffmann-La Roche Inc., Nutley, N.J.

[21] Appl. No.: 317,259

[22] Filed: Oct. 3, 1994

[30] Foreign Application Priority Data

Oct. 22, 1993 [CH] Switzerland ............... 3201/93

[51] Int. Cl.$^6$ ............ A61K 31/40; C07D 209/04
[52] U.S. Cl. ............ 514/415; 514/418; 548/469; 548/484; 548/485; 548/486
[58] Field of Search ............... 548/469, 484, 548/485, 486; 514/415, 418

[56] References Cited

FOREIGN PATENT DOCUMENTS 2097465  6/1993  Canada .
0572863  8/1993  European Pat. Off. .

OTHER PUBLICATIONS

CA 97:92759h Amino . . . Use. Geiger et al., p. 819, 1982.
CA 66:94861u 2-Aminoethylation . . . –Indole. Pfeil et al., p. 8874, 1967.
CA 102: 149796w N–Alkylated . . . Esters. Henning et al., p. 664, 1985.
CA 109: 38242n Preparation . . . Senescence. Vincent et al., p. 660, 1988.
CA 110:185342u Molecular . . . Recognition. Hadzi et al., p. 17, 1989.
CA 112:199014s Molecular . . . Recognition. Hadzi et al., p. 780, 1990.
J. Het. Chem. 16, 221–224 (1979).
Proc. Roy. Soc. London, 148B, 481–494 (1958).
Bull. Soc. Chim. France, 1978, 651.
S. J. Peroutka, Biol. Psychiatry, 20 971–979 (1985).
A. Pazos et al., Europ. J. Pharmacol. 106, 539–546 (1984).
D. Hoyer, Receptor Research 8, 59–81 (1988).
J. E. Leysen, Molecular Pharmacology 21, 301–314 (1981).
S. J. Peroutka e al., Brain Research 584, 191–196 (1992).
T. Branchek et al., Molecular Pharmacology 38, 604–609 (1990).
Berendensen & Broekkamp, Eur. J. Pharmacol. 135, 279–287 (1987).
Knitel, Synthesis p. 186 (1985).

Primary Examiner—Joseph K. McKane
Attorney, Agent, or Firm—George M. Gould; William H. Esptein; Raina Semionow

[57] ABSTRACT

The invention releates to indole derivatives of the formula

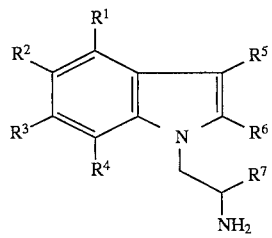

wherein $R^1$ to $R^4$ are, independently, hydrogen, halogen, lower-alkyl, cycloalkyl or trifluoromethyl, $R^5$ and $R^6$ are, independently, hydrogen, halogen, lower-alkyl, cycloalkyl, trifluoromethyl, hydroxy or lower-alkoxy and $R^7$ is hydrogen or lower-alkyl, and pharmaceutically acceptable acid addition salts thereof.

The compounds of formula I bind to serotonin receptors and are therefore useful in the treatment and/or prevention of central nervous system disorders, such as depression.

7 Claims, No Drawings

INDOLE DERIVATIVES

SUMMARY OF THE INVENTION

The invention relates to indole derivatives of the formula

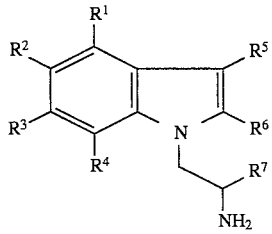

wherein $R^1$ to $R^4$ are, independently, hydrogen, halogen, lower-alkyl, cycloalkyl or trifluoromethyl, $R^5$ and $R^6$ are, independently, hydrogen, halogen, lower-alkyl, cycloalkyl, trifluoromethyl, hydroxy or lower-alkoxy and $R^7$ is hydrogen or lower-alkyl, and pharmaceutically acceptable acid addition salts of the compounds of formula I.

The compounds of formula I and their salts are distinguished by valuable therapeutic properties.

In particular, the compounds of formula I are useful for the treatment or prevention of central nervous disorders, such as, depression. The compounds of formula I can also be used for the treatment of bipolar disorders, anxiety states, sleep and sexual disorders, psychoses, schizophrenia, migraine and other conditions associated with cephalic pain or pain of a different kind, personality disorders or obsessive-compulsive disorders, social phobias or panic states, mental organic disorders, mental disorders in childhood, aggressiveness, age-associated memory impairment and behavioral disorders, addiction, obesity, bulimia and the like; central nervous system damage caused by trauma, stroke, neurodegenerative diseases and the like; and cardiovascular disorders, such as, hypertension, thrombosis, stroke, and gastrointestinal disorders, such as, dysfunction of the gastrointestinal tract motility.

In another aspect, the invention relates to compounds of the formula

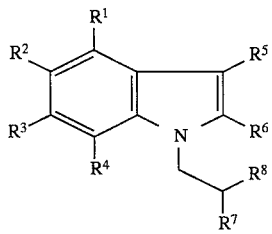

wherein $R^1$ to $R^7$ have the significance given above and $R^8$ is a residue convertible Into an amino group, a leaving group or a hydroxy group.

DETAILED DESCRIPTION OF THE INVENTION

The invention relates to indole derivatives of the formula

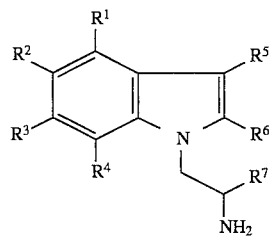

wherein $R^1$ to $R^4$ are, independently, hydrogen, halogen, lower-alkyl, cycloalkyl or trifluoromethyl, $R^5$ and $R^6$ are, independently, hydrogen, halogen, lower-alkyl, cycloalkyl, trifluoromethyl, hydroxy or lower-alkoxy and $R^7$ is hydrogen or lower-alkyl, and pharmaceutically acceptable acid addition salts of the compounds of formula I.

In particular, the compounds of formula I are useful for the treatment or prevention of central nervous disorders, such as, depression. The compounds of formula I can also be used for the treatment of bipolar disorders, anxiety states, sleep and sexual disorders, psychoses, schizophrenia, migraine and other conditions associated with cephalic pain or pain of a different kind, personality disorders or obsessive-compulsive disorders, social phobias or panic states, mental organic disorders, mental disorders in childhood, aggressiveness, age-associated memory impairment and behavioral disorders, addiction, obesity, bulimia and the like; central nervous system damage caused by trauma, stroke, neurodegenerative diseases and the like; and cardiovascular disorders, such as, hypertension, thrombosis, stroke, and gastrointestinal disorders, such as, dysfunction of the gastrointestinal tract motility.

Objects of the invention are the compounds of formula I and pharmaceutically acceptable acid addition salts thereof, the preparation of the compounds of formula I and salts thereof, medicaments containing a compound of formula I or a as pharmaceutically acceptable acid addition salt thereof, the manufacture of such medicaments and the use of the compounds of formula I and their pharmaceutically acceptable salts in the control or prevention of illnesses, especially of illnesses and disorders of the kind referred to earlier, and, respectively, for the manufacture of corresponding medicaments.

Furthermore, the invention also relates to the compounds of the formula:

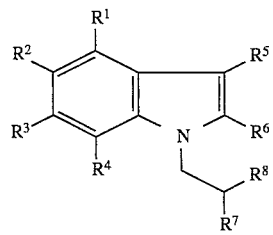

wherein $R^1$ to $R^7$ have the significance given above and $R^8$ is a residue convertible into an amino group, a leaving group or a hydroxy group.

These compounds of formula II are important intermediates for the preparation of the pharmaceutically valuable compounds of formula I.

The term "lower" denotes residues with a maximum of 7, preferably up to 4, carbon atoms; "alkyl" denotes straight-chain or branched, saturated hydrocarbon residues, such as, methyl, ethyl, isopropyl or t-butyl; and alkoxy denotes an alkyl group bonded via an oxygen atom, such as methoxy, ethoxy, propoxy, isopropoxy or s butoxy. "Halogen" is Cl, Br, F or I.

The term "pharmaceutically acceptable acid addition salts" embraces salts with inorganic and organic acids, such as, hydrochloric acid, hydrobromic acid, nitric acid, surfuric acid, phosphoric acid, citric acid, formic acid, fumaric acid, maleic acid, acetic acid, succinic acid, tartaric acid, methanesulfonic acid, p-toluenesulfonic and the like.

$R^7$ can conveniently be lower-alkyl, preferably methyl. Compounds in which $R^7$ is hydrogen are also preferred. When $R^7$ is methyl, compounds in which $R^5$ and $R^6$ are hydrogen are especially preferred.

Furthermore, compounds in which $R^1$ is hydrogen or methyl, $R^2$ is hydrogen or fluorine, $R^3$ is hydrogen or chlorine and $R^4$ is hydrogen are preferred.

Some particularly preferred representatives of the class of substance defined by formula I in the scope of the invention are:

2-( 5-Fluoroindol-1-yl)-ethylamine;
2-( 6-chloro-5-fluoro-indol-1-yl)-ethylamine;
2-( 4-methyl-3-methoxy-indol-1-yl)-ethylamine; and
(RS)-2-( 6-chloro-5-fluoro-indol-1-yl)-1-methyl-ethylamine.

Examples of other preferred compounds of formula I are:
2-(4-Chloro-5-fluoro-3-methoxy-indol-1-yl)-ethylamine;
2-(5-fluoro-3-methoxy-indol-1-yl)-ethylamine;
2-(5-chloro-indol-1-yl)-ethylamine;
2-(4-chloro-5-fluoro-indol-1-yl)-ethylamine;
(RS)-2-(5-chloro-indol-1-yl)-1-methyl-ethylamine;
(RS)-2-(5-fluoro-indol-1-yl)-1-methyl-ethylamine;
(RS)-2-(6-chloro-5-fluoro-indol-1-yl)-1-methyl-ethyl amine;
(R)-2-(5-fluoro-indol-1-yl)-1-methyl-ethylamine;
(S)-2-(6-chloro-5 -fluoro-indol-1-yl)-1-methyl-ethylamine;
(R)-2-(6-chloro-5-fluoro-indol-1-yl)-1-methyl-ethylamine;
(RS)-2-(4-methyl-indol-1-yl)-1-methyl-ethylamine;
(RS)-2-(5-bromo-indol-1-yl)-1-methyl-ethylamine;
(RS)-2-(6-fluoro-indol-1-yl)-1-methyl-ethylamine;
(S)-2-(5,6-difluoro-indol-1-yl)-1-methyl-ethylamine;
(R)-2-(5,6-difluoro-indol-1-yl)-1-methyl-ethylamine;
(S)-2-(5-fluoro-4-trifluoromethyl-indol-1-yl)-1-methyl-ethylamine;
(S)-2-(5-fluoro-6-trifluoromethyl-indol-1-yl)-1-methyl-ethylamine;
(S)-2-(4-chloro-5-fluoro-indol-1-yl)-1-methyl-ethylamine; and
(R)-2-(4-chloro-5-fluoro-indol-1-yl)-1-methyl-ethylamine.

The compounds of formula I as well as their pharmaceutically acceptable acid addition salts can be prepared in accordance with the invention by a) converting a compound of the formula

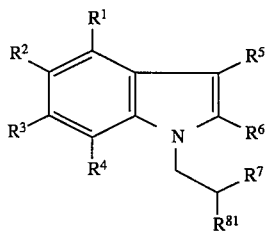

IIa wherein $R^1$ to $R^7$ have the significances given above and $R^{81}$ is a residue convertible into a amino group, into the corresponding amino compound, or b) reacting a compound of the formula

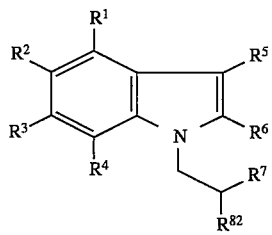

IIb wherein $R^1$ to $R^7$ have the significances given above and $R^{82}$ is a leaving group,
with ammonia; and c) if desired, converting the compound of formula I obtained into a pharmaceutically acceptable acid addition salt.

The compounds of formula IIa in which $R^{81}$ is a residue convertible into an amino group, preferably an azido group, but also a nitro group, can be prepared according to known methods.

When $R^{81}$ is an azido group, the compounds of formula I are prepared by reduction. This reduction can be carried out with complex hydrides, for example, lithium aluminum hydride or by catalytic hydrogenation on metal catalysts, for example, platinum or palladium. When lithium aluminum hydride is used as the reducing agent, anhydrous ether or tetrahydrofuran are suitable as the solvent. The reduction can be conveniently carried out as follows: after the dropwise addition of the compound IIa wherein $R^{81}$ is $N_3$ to a solution consisting of the anhydrous solvent and the hydride, the mixture is boiled at reflux, subsequently hydrolyzed with aqueous ether or THF solution and the aluminum hydroxide and lithium hydroxide precipitate is extracted with THF.

The catalytic hydrogenation on metal catalysts, for example, platinum or palladium, is effected at room temperature. Especially suitable solvents are: water, alcohols, such as, methanol, ethenol and the like, ethyl acetate, dioxane, glacial acetic acid or mixture of these solvents.

The hydrogenation is effected under a hydrogen atmosphere either in an autoclave or in a shaking apparatus.

Compounds of formula I can also be prepared when compounds of formula IIb in which $R^{82}$ is a leaving group, for example, halogen, especially bromine, are reacted with ammonia.

The compounds of formula IIb are conveniently suspended in liquid ammonia and stirred in an autoclave while heating. After evaporation of the ammonia, the residue is taken up in a solvent, preferably dichloromethane, washed and dried.

It has been found that the acid addition salts of these compounds are especially well suited for pharmaceutical use. Compounds of formula I in the form of fumaric acid salts are particularly suitable, although all other acids mentioned in the description form pharmaceutically acceptable acid addition salts.

The addition of the corresponding acids to the compounds of formula I is conveniently effected before their ultimate isolation at the conclusion of the described process variant.

The indole derivatives which are used as starting materials for the preparation of the compounds of formula IIa and IIb can be prepared, for example, by known methods according to the following Reaction Schemes, for example, according to the Fischer indole synthesis, where arylhydrazones of aldehydes or ketones are cyclized under the influence of acids or metal hydrides as the catalyst with the cleavage of ammonia:

Scheme 1

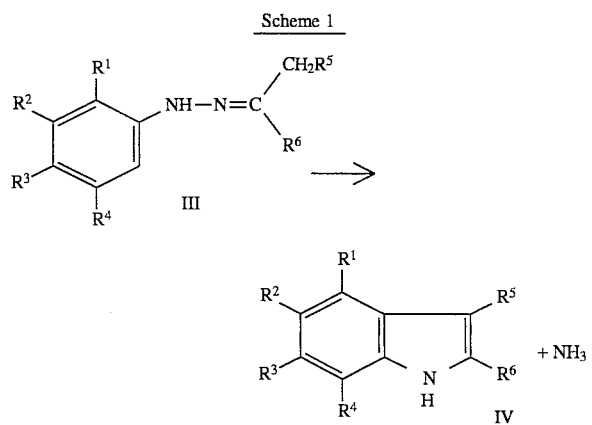

In this, the substituents $R^1$ to $R^6$ have the above significance.

Corresponding indole derivatives can also be prepared according to the following Scheme in analogy to processes described in Synthesis, 1985, p. 186:

Scheme 2

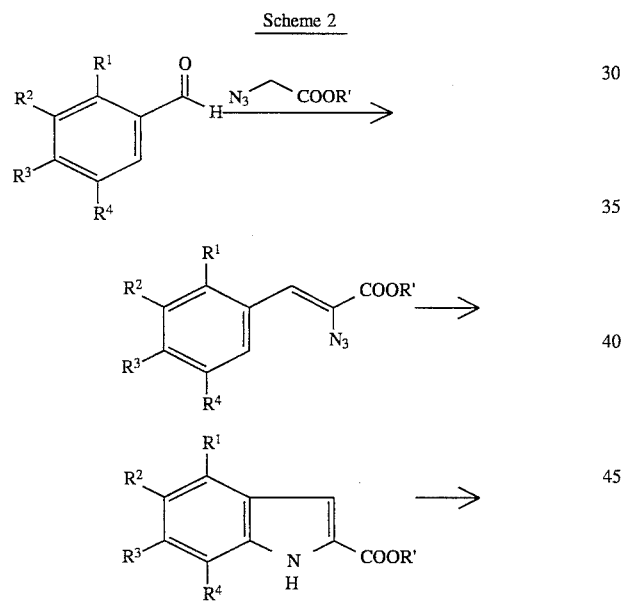

-continued
Scheme 2

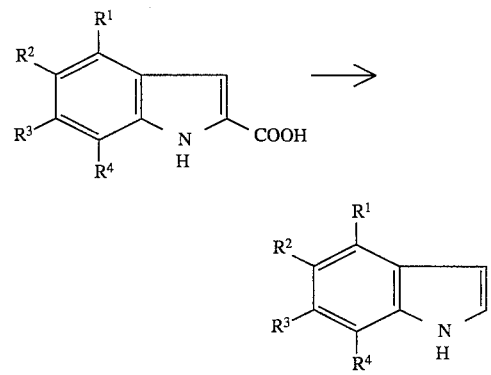

In this, $R^1$ to $R^4$ have the significances given above and R' is lower-alkyl.

Aromatic aldehydes are converted into alkyl a-azidocinnamates by an alkoxide-catalyzed condensation with alkyl azidoacetates in a one-stage reaction and in good yields.

A thermolysis in boiling p-xylene subsequently leads in almost quantitative yield to alkyl indole-2-carboxylates. The ester group can be hydrolyzed according to known methods and the acid group can be cleaved off thermally.

Furthermore, indole compounds can be obtained when a correspondingly substituted phenylglycine is cyclized, as Scheme 3 hereinafter shows:

Scheme 3

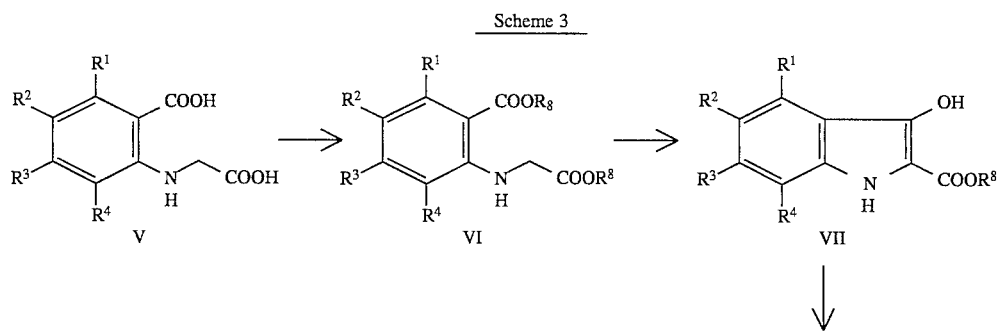

Scheme 3 -continued

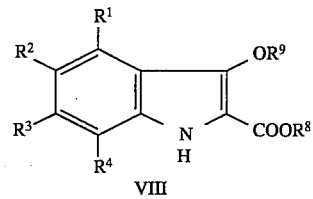

$R^1$ to $R^4$ have the significances given above and $R^8$ and $R^9$ are lower alkyl, whereby $R^8$ and $R^9$ can be the same or different.

The compounds of formula V can be converted into the compounds of formula VI with alcohols according to known methods. By cyclizing a compound of formula VI, there is obtained an indole of formula VII (J. Het. Chem. 16, 221 (1979)). The compounds of formula VIII are obtained by reacting an indole of formula VII with an alkylating agent, for example, with a dialkyl sulfate or with diazomethane. This reaction is effected in alcoholic solvents, preferably methanol, at room temperature.

Reaction Scheme 4 shows another method for the preparation of corresponding indoles as starting materials for the preparation of the compounds of formula I.

In this case also, the preparation starts from a correspondingly substituted phenyl glycine of formula V.

A compound of formula V can be converted with an acetate, preferably sodium acetate, in acetic anhydride under reflux, into a compound of formula IX, which can be converted by hydrolysis, for example, with concentrated surfuric acid, into a compound of formula X. The compounds of formula X are known (see Proc. Roy. Soc. London, 178 B, 781 (195 8 ) ) or can be prepared in an analogous manner.

Alkylation of a compound of formula X can be effected with conventional alkylating agents, for example, dialkyl sulfates. Methylation is preferably effected with dimethyl sulfate to a compound of formula XI analogously to the disclosure appearing in Bull. Soc. Chem. France 1978, 651.

The cleavage of the N-acetyl group can be effected using conventional methods, for example by reaction with a sodium alcoholate in an alcoholic solvent, preferably sodium methylate in methanol.

Scheme 4

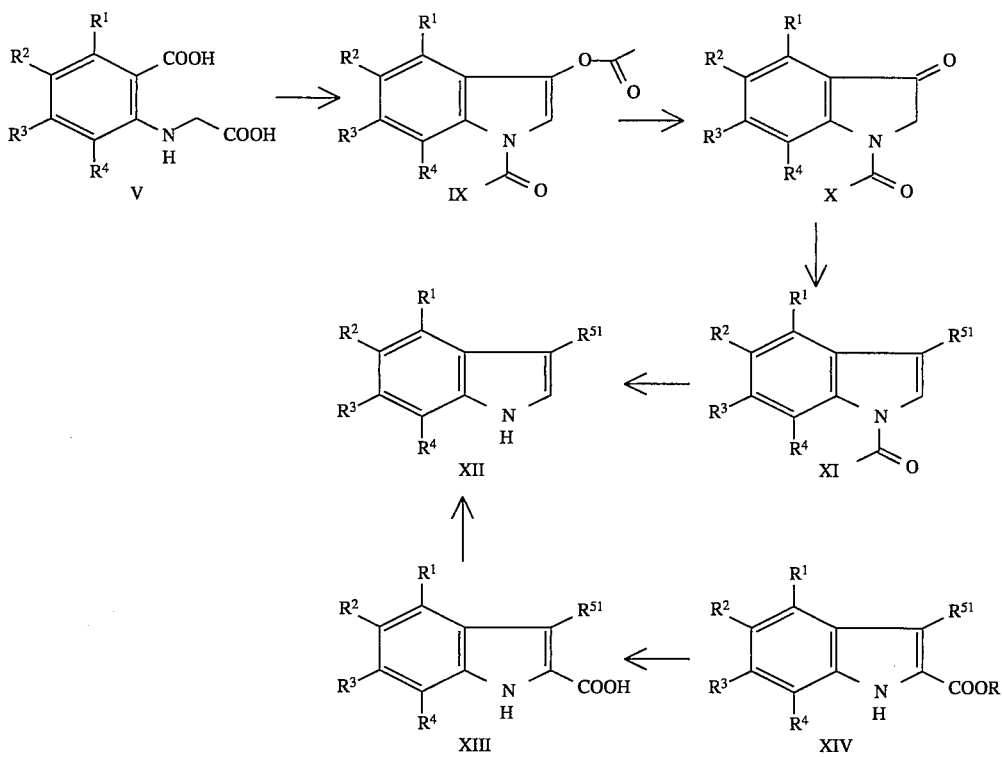

The substituent designations for $R^1$ to $R^4$ correspond to those given above, $R^{51}$ is lower-alkoxy and R is lower-alkyl.

Another possibility for the preparation of the compounds of formula XII comprises hydrolyzing the indole esters of formula XIV to the acids of formula XIII. Alkali hydroxide is conveniently used for this purpose.

The decarboxylation of the compounds of formula XIII to the corresponding compounds of formula XII can be effected by the action of temperatures between 300° to 320° C. in a metal bath.

The compounds of formula II are prepared according to Scheme 5 starting from the described indole compounds of formula IV.

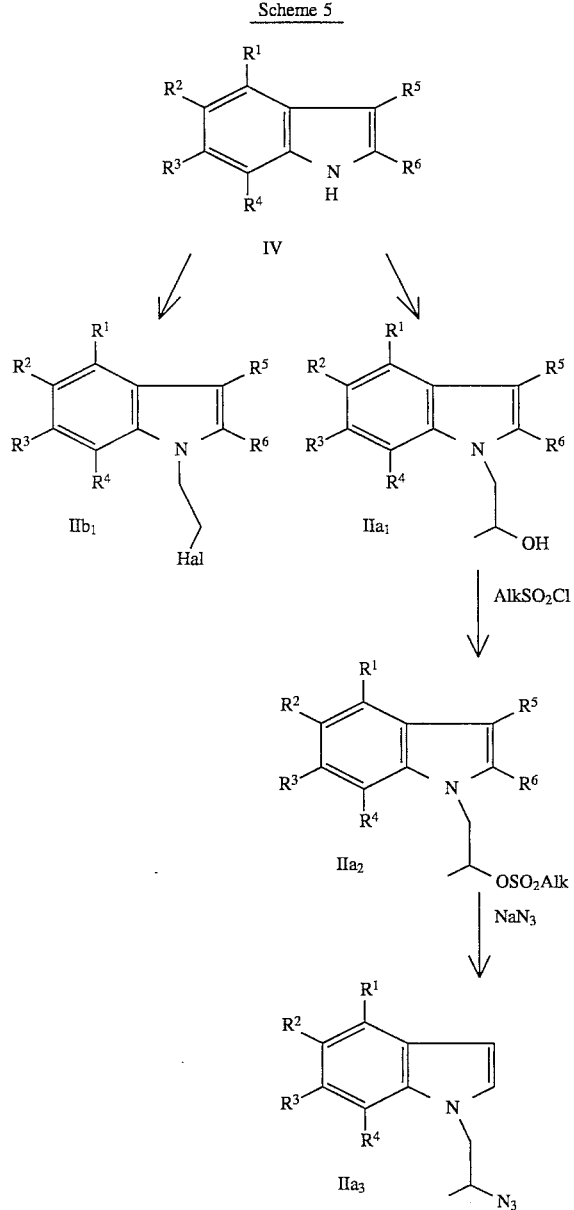

Scheme 5

In Reaction Scheme 5, $R^1$ to $R^6$ have the significances given above.

A compound of formula IIb$_1$ is obtained by treating a compound of formula IV with a suitable alkylating agent, preferably 1,2-dibromoethane. This reaction is conveniently carried out under conditions utilized for phase transfer catalysis. Such a reaction is effected while stirring in a two-phase system of water and a water-immiscible organic solvent in the presence of a strong base and a phase transfer catalyst. 1,2-Dibromoethane, when it simultaneously serves as the reagent, can conveniently be used as the organic solvent. A suitable strong base is, for example, potassium hydroxide or sodium hydroxide. The conventional phase transfer catalysts can be used. Suitable catalysts are, for example, benzyltrimethyl-ammonium chloride, tetrabutylammonium bromide and similar compounds. The reaction is preferably carried out at a temperature in the range of about 20° to 80° C.

The compound of formula IIa$_1$ can be prepared, for example, by reacting compounds of formula IV with an epoxide.

The compounds of formula IV can preferably be dissolved at about 0° C. in a suspension consisting of sodium hydride and tetra-hydrofuran and subsequently treated with an alkyloxirane, to give the corresponding compounds of formula IIa$_1$.

The hydroxy group can be replaced by a leaving group according to known methods, for example, by reaction with a sulfonyl chloride, preferably with methanesulfonyl chloride, to give o the sulfonate. Compounds of formula IIa$_2$ or IIb$_1$ can be converted into the corresponding azido compounds by treatment with an azide, preferably sodium azide, in a polar solvent such as, for example, DMF.

As mentioned earlier, the compounds of formula I and their pharmaceutically usable acid addition salts possess valuable pharmacodynamic properties. They have the capacity to bind to serotonin receptors and are accordingly suitable for the treatment or prophylaxis of illnesses and disorders of the kind referred to earlier and, respectively, for the preparation of corresponding medicaments.

The binding of a compound of formula I to serotom receptors was determined in vitro by standard methods. The preparations were investigated in accordance with the tests given hereinafter:

METHOD 1 a) For the binding to the 5HT$_{1A}$ receptor in accordance with the $^3$H-8-OH-DPAT binding assay according to the method of S. J. Peroutka, Biol. Psychiatry 20, 971–979 (1985).

b) For the binding to the 5HT$_{2C}$ receptor in accordance with the $^3$H-mesulergin binding assay according to the method of A.Pazos et al., Europ. J. Pharmacol. 106, 539–546 or D.Hoyer, Receptor Research 8, 59–81 (1988).

c) For the binding to the 5HT$_{2A}$ receptor in accordance with the $^3$H-ketanserine binding assay according to the method of J. E.Leysen, Molecular Pharmacology 21, 301–304 (198 1 ).

The IC$_{50}$ values of the test substances were determined, that is, the concentration in nmol by which 50% of the receptor-bound ligands are displaced.

The thus-determined activity of some compounds in accordance with the invention as well as those of some comparative compounds will be evident from the following Table:

| Substance | Test method | | |
|---|---|---|---|
| | a | b | c |
| Buspirone | 19.50 | 3700.0 | 990.0 |
| NAN-190 | 0.56 | 1800.0 | 581.0 |
| 5HT | 1.50 | 9.5 | 1730.0 |
| Metergoline | 4.80 | 5.5 | 64.9 |
| mCPP | 227.00 | 53.0 | 319.0 |
| RU 24969 | 8.00 | 159.0 | 2500.0 |
| CP93129 | 1620.00 | 2780.0 | 29200.0 |
| Ritanserine | 5740.00 | 37.0 | 3.1 |
| Pirenperone | 2870.00 | 37.0 | 12.9 |

-continued

| Substance | Example | Test method | | |
|---|---|---|---|---|
| | | a | b | c |
| A | 1 | 1300 | 87 | 1580 |
| B | 2 | 3330 | 43 | 573 |
| C | 3 | 5070 | 533 | 6330 |
| D | 4 | 309 | 194 | 2720 |
| E | 5 | 3680 | 23,5 | 320 |
| F | 6 | 3470 | 32 | 1310 |
| G | 7 | 2370 | 64 | 850 |
| H | 8 | 5650 | 63 | 2490 |
| I | 9 | 7220 | 81 | 740 |
| J | 10 | 2420 | 13.5 | 922 |
| K | 11 | 5070 | 113 | 1340 |
| L | 12 | inact. | 75 | 1430 |
| M | 14 | 3080 | 9.5 | 860 |
| N | 13 | 1570 | 44.5 | 893 |
| O | 15 | 8650 | 77 | 1140 |
| P | 16 | 4060 | 168 | 4000 |
| U | 24 | 5590 | 25 | 403 |
| Q | 18 | 2430 | 58 | 2700 |
| R | 20 | inact. | 47 | 2120 |
| S | 19 | 5010 | 94 | 3260 |
| T | 23 | 9450 | 14 | 402 |
| V | 25 | 4740 | 629 | 5060 |

A 2-(5-Fluoro-indol-1-yl)-ethylamine fumarate.
B 2-(4-Chloro-5-fluoro-3-methoxy-indol-1-yl)-ethylamine fumarate.
C 2-(5-Fluoro-3-methoxy-indol-1-yl)-ethylamine fumarate.
D 2-(5-Chloro-indol-1-yl)-ethylamine fumarate.
E 2-(4-Chloro-5-fluoro-indol-1-yl)-ethylamine fumarate.
F 2-(6-Chloro-5-fluoro-indol-1-yl)-ethylamine fumarate.
G 2-(4-Methyl-3-methoxy-indol-1-yl)-ethylamine fumarate.
H (RS)-2-(5-Chloro-indol-1-yl)-1-methyl-ethylamine fumarate.
I (RS)-2-(5-Fluoro-indol-1-yl)-1-methyl-ethylamine fumarate.
J (RS)-2-(6-Chloro-5-fluoro-indol-1-yl)-1-methyl-ethylamine fumarate.
K (R)-2-(5-Fluoro-indol-1-yl)-1-methyl-ethylamine fumarate.
L (S)-2-(5-Fluoro-indol-1-yl)-1-methyl-ethylamine fumarate.
M (S)-2-(6-Chloro-5-fluoro-indol-1-yl)-1-methyl-ethylamine fumarate.
N (R)-2-(6-Chloro-5-fluoro-indol-1-yl)-1-methyl-ethylamine fumarate.
O (RS)-2-(4-Methyl-indol-1-yl)-1-methyl-ethylamine fumarate.
P (RS)-2-(5-Bromo-indol-1-yl)-1-methyl-ethylamine fumarate.
Q (RS)-2-(6-Fluoro-indol-1-yl)-1-methyl-ethylamine fumarate.
R (S)-2-(5,6-Difluoro-indol-1-yl)-1-methyl-ethylamine fumarate.
S (R)-2-(5,6-Difluoro-indol-1-yl)-1-methyl-ethylaraine fumarate.
T (S)-2-(4-Chloro-5-fluoro-indol-1-yl)-1-methyl-ethylamine fumarate.
U (R)-2-(4-Chloro-5-fluoro-indol-1-yl)-1-methyl-ethylamine fumarate.
V (RS)-2-(5-Methyl-indol-1-yl)-1-methyl-ethylamine fumarate.

METHOD II a) Displacement tests with [3H]-5-HT(1 nM) as the radioligand on recombinant human-5HT$_{1A}$ receptors expressed in 3T3 cells of mice were carried out in order to determine the affinity of a compound to the 5HT$_{1A}$ receptor. Membranes which had been obtained from $2 \times 10^5$ cells were used as were various concentrations of the respective test compound.

b) For the binding to the 5HT$_{2C}$ receptor, in accordance with the [3H]-5-HT binding assay according to the method of S. J. Peroutka et al., Brain Research 584, 191–196 (1992).

c) For the binding to the 5HT$_{2A}$ receptor, in accordance with the [3H]-DOB binding assay according to the method of T. Branchek et al., Molecular Pharmacology 38, 604–609 (1990).

The pki values (pki=—log10 Ki) of the test substances are given. The ki value is defined by the following formula:

$$Ki = \frac{IC_{50}}{1 + \frac{[L]}{K_D}}$$

in which the IC$_{50}$ values are those concentrations of test compound in nM by which 50% of the receptor-bound ligands are displaced. [L] is the concentration of ligand and the K$_D$ value is the dissociation constant of the ligand.

The thus-determined activity of some compounds in accordance with the invention will be evident from the following Table:

| Example No. | Test method | | |
|---|---|---|---|
| | a | b | c |
| 30 | 5.00 | 8.40 | 6.73 |
| 31 | 5.50 | 7.91 | 6.61 |
| 32 | 6.16 | 8.21 | 6,59 |
| 33 | 5.00 | 8.46 | 6.91 |
| 34 | 5.00 | 8.81 | 7.49 |
| 35 | 5.00 | 8.28 | 6.86 |
| 36 | 5.30 | 8.52 | 7.12 |
| 37 | 4.98 | 8.57 | 8.50 |
| 38 | <5 | 7.70 | 6.80 |

In this Table the respective compounds are:
30 (S)-2-(2-Ethyl-5-fluoroindol-1-yl)-1-methyl-ethylamine fumarate,
31 (S)-2-(4-isopropyl-5-fluoroindol-1-yl)-1-methyl-ethylamine fumarate,
32 (S)-2-(6-isopropyl-5-fluoroindol-1-yl)-1-methyl-ethylamine fumarate,
33 (S)-2-(6-chloro-5-fluoro-3-ethylindol-1-yl)-1-methyl-ethylamine fumarate,
34 (S)-2-(4-chloro-5-fluoro-3-ethylindol-1-yl)-1-methyl-ethylamine fumarate,
35 (S)-1-methyl-2-(5-fluoro-3-methylindol-1-yl)-ethylamine fumarate,
36 (S)-2-(6-chloro-5-fluoro-3-methylindol-1-yl)-1-methyl-ethylamine fumarate,
37 (S)-2-(5-fluoro-3-methoxy-4-methylindol-1-yl)-1-methyl-ethylamine fumarate,
38 (S)-2-(3-methoxy-4-methylindol-1-yl)-1-methyl-ethylamine fumarate.

PENILE ERECTION (RATS)

It has been shown that penile erection is dependent on the stimulation of the 5HT$_{2C}$ receptor (see Berendsen & Broekkamp, Eur. J.Pharmacol, 135, 179184 (1987)).

The number of penile erections was determined within 45 minutes following administration of the test substance to the animal. The ED$_{50}$ is that dosage which brings about 50% of these erections.

| Example No. | ED$_{50}$ (mg/kg, s.c.) |
| --- | --- |
| 1 | 0.49 |
| 2 | 0.23 |
| 3 | 2.70 |
| 4 | 3.30 |
| 5 | 0.27 |
| 6 | 0.30 |

The compounds of formula I and the pharmaceutically acceptable acid addition salts of the compounds of formula I can be used as medicaments, for example, in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, for example, in the form of suppositories, parenterally, for example, in the form of injection solutions, or nasally.

For the preparation of pharmaceutical dosage foes, the compounds of formula I and the pharmaceutically acceptable acid addition salts of the compounds of formula I can be processed with pharaceutically inert, inorganic or organic carriers. Lactose, corn starch or derivatives thereof, talc, stearic acid or its salts and the like can be used, for example, carriers for tablets, coated tablets, dragées and hard gelatin capsules. Suitable carriers for soft gelatin capsules are, for example, vegetable oil, waxes, fats, semi-solid and liquid polyols and the like. Depending on the nature of the active substance no carriers are, however, usually required in the case of soft gelatine capsules. Suitable carriers for the preparation of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances.

Medicaments containing a compound of formula I or a pharmaceutically acceptable acid addition salt thereof and a therapeutically inert carrier are also an object of the invention, as is a process for preparing them which comprises bringing one or more compounds of formula I and/or pharmaceutically acceptable acid addition salts thereof into a galenical form for administration together with one or more therapeutically inert carriers.

In accordance with the invention, compounds of formula I as well as their pharmaceutically acceptable acid addition salts are useful in the treatment or prevention of central nervous disorders such as depressions. The compounds of formula I can also be used for the treatment of bipolar disorders, anxiety states, sleep and sexual disorders, psychoses, schizophrenia, migraine and other conditions associated with cephalic pain or pain of a different kind, personality disorders or obsessive-compulsive disorders, social phobias or panic states, mental organic disorders, mental disorders in childhood, aggressiveness, age-associated memory impairment and behavioural disorders, addiction, obesity, bulimia and the like; central nervous system damage caused by trauma, stroke, neurodegenerative diseases and the like; cardiovascular disorders, such as, hypertension, thrombosis, stroke and the like; and gastrointestinal disorders, such as, disfunction of the gastrointestinal tract motility, and, respectively, for the preparation of the corresponding medicaments. The dosage can vary within wide limits and will, of course, be fitted to the individual requirements in each particular case. In the case of oral administration, the dosage is in a range of about 0.01 mg per dosage to about 500 mg per day of a compound of formula I or the corresponding mount of a pharmaceutically acceptable acid addition salt thereof, although the upper limit can also be exceeded when this is shown to be indicated.

The following Examples illustrate the invention in more detail. All temperatures are given in degrees Celsius.

EXAMPLE 1

A solution of 9.8 g of 5-fluoroindole in 360 ml of 1,2-dibromoethane was treated with 180 ml of 28% NaOH and 0.59 g of tetrabutylammonium bromide. The mixture was stirred at 50° for 42 hours. The phases were separated and the aqueous phase was extracted with toluene. The combined organic phases were washed with water and dried over sodium sulfate. The solvent was distilled off and the residue was suspended in 1.9 l of liquid ammonia and stirred in an autoclave at 80° for 15 hours. After evaporation of the ammonia the residue was taken up in 500 ml of dichloromethane and washed with 100 ml of water and 100 ml of saturated sodium chloride solution. The organic phase was dried over sodium surfate and the solvent was distilled off. The residue was chromatographed over 350 g of silica gel with ethyl acetate-methanol (5:1). There were obtained 8.6 g of a reddish oil which was dissolved in 970 ml of ether and treated with active charcoal. After filtration the solution was treated with 5.6 g of fumaric acid and stirred for 2 days. The crystals were filtered off and dried. There were obtained 11.1 g (39.5%) of 2-(5-fluoro-indol-1-yl)-ethylamine fumarate (1:1.8) with m.p. 173°–175° (dec.)

EXAMPLE 2 a) A suspension of 2.63 g of N-[3-chloro-2-(hydroxycarbonyl)-4-fluoro-phenyl]glycine and 2.63 g of sodium acetate in 25 ml of acetic anhydride was boiled under reflux for 45 minutes. The solvent was removed in a vacuum and the residue was treated with 50 ml of water. The crystals were filtered off, washed with water and dried. There were obtained 2.7 g (94%) of 3-acetoxy-1-acetyl-4-chloro-5-fluoroindole as yellow crystals with m.p. 168°–169°.

b) 2.65 g of 3-acetoxy-1-acetyl-4-chloro-5-fluoroindole were added to 20 ml of 90% surfuric acid and the reaction mixture, after stirring for three quarters of an hour, was diluted with 100 ml of ice-water. The precipitate was filtered off, washed with water and dried. There were obtained 2 g (92.5%) of 1-acetyl-4-chloro-5-fluoroindolin-3-one as pale brown crystals with a m.p. of 203°–204°.

c) A mixture of 2 g of 1-acetyl-4-chloro-5-fluoroindolin-3-one, 2 g of powdered sodium hydroxide and 30 ml of dimethyl sulfate was stirred at room temperature for 5 hours. After the addition of 250 ml of saturated sodium bicarbonate solution the mixture was stirred overnight and subsequently filtered. The residue was filtered in 150 ml of ether and 100 ml of ethyl acetate. The solution was dried over sodium sulfate, filtered and evaporated. There were obtained 2 g (95%) of 1-acetyl-4-chloro-5-fluoro-3-methoxyindole as greenish crystals with m.p. 114°–115°.

d) A solution of 2 g of 1-acetyl-4-chloro-5-fluoro-3-methoxyindole and 0.48 of sodium methylate in 35 ml of methanol was stirred at room temperature for one hour. After removal of the solvent the residue was extracted with water and ethyl acetate and the organic phase was washed with saturated sodium chloride solution and dried over sodium sulfate. The solvent was removed and the residue was chromatographed over 100 g of silica gel with hexane-ethyl acetate (3:1). 0.88 g (53%) of 4ochloro-5-fluoro-3-methoxyindole was obtained.

e) A solution of 2 g of 4-chloro-5-fluoro-3-methoxyindole in 50 ml of 1,2-dibromoethane was treated with 50 ml of 28% NaOH and 100 mg of tetrabutyl-ammonium bromide. The mixture was stirred is for 15 hours. The phases were separated and the aqueous phase was extracted with toluene. The combined organic phases were washed with water and dried over sodium sulfate. The solvent was distilled off and the residue was suspended in 200 ml of liquid ammonia and stirred in an autoclave at 80° for 18 hours. After evaporation of the ammonia the residue was taken up in 50 ml of dichloromethane and washed with water and saturated sodium chloride solution. The organic phase was dried over sodium sulfate and the solvent was distilled off. The residue was dissolved in 200 ml of ether and treated with 0.7 g of fumaric acid and stirred for 2 days. The crystals were isolated and dried. There were obtained 2 g (55%) of 2-(4-chloro-5-fluoro-3-methoxy-indol-1-yl)-ethylamine fumarate (1:1) as beige crystals with m.p. 195°–196°.

EXAMPLE 3 a) 2.2 g of 3-acetoxy-1-acetyl-5-fluoroindole were added to 20 ml of 90% sulfuric acid and, after stirring for three quarters of an hour, the reaction mixture was diluted with 100 ml of ice-water. The precipitate was filtered off, washed with water and dried. There were obtained 1.6 g (83%) of 1-acetyl-5-fluoroindolin-3-one as beige crystals with a m.p. of 143°–144°.

b) A mixture of 1.6 g of 1-acetyl-5-fluoroindolin-3-one, 1.9 g of powdered sodium hydroxide and 28 ml of dimethyl sulfate was stirred at room temperature for two hours. After the addition of 240 ml of saturated sodium bicarbonate solution the mixture was stirred overnight and subsequently filtered. The residue was taken up in 100 ml of ether and 100 ml of ethyl acetate. The solution was dried over sodium sulfate, filtered and evaporated. There were obtained 1.47 g (86%) of 1-acetyl-5-fluoro-3-methoxyindole as greenish crystals with m.p. 124°–125°.

c) A solution of 1.25 g of 1-acetyl-5-fluoro-3-methoxyindole and 0.35 g of sodium methylate in 23 ml of methanol was stirred at room temperature for one hour. After removal of the solvent the residue was extracted with water and ethyl acetate and the organic phase was washed with saturated sodium chloride solution and dried over sodium sulfate. The solvent was removed and the residue was distilled in a bulb-tube at a bath temperature of 200° and a pressure of 50 mbar. 0.76 g (76%) of 5-fluoro-3-methoxyindole was obtained.

d) A solution of 0.76 g of 5-fluoro-3-methoxyindole in 25 ml of 1,2-dibromoethane was treated with 25 ml of 28% NaOH and 40 mg (0.12 mmol) of tetrabutyl-ammonium bromide. The mixture was stirred at 50° for 15 hours. The phases were separated and the aqueous phase was extracted with toluene. The combined organic phases were washed with water and dried over sodium sulfate. The solvent was distilled off and the residue was chromatographed over 60 g of aluminium oxide with hexane-ethyl acetate (5:1). There was obtained a yellow oil which was suspended in 80 ml of liquid ammonia and stirred in an autoclave at 80° for 18 hours. After evaporation of the ammonia the residue was taken up in dichloromethane and washed with water and saturated sodium chloride solution. The organic phase was dried over sodium surfate and the solvent was distilled off. The residue was dissolved in 90 ml of ether and 3 ml of methanol and treated with 0.35 g of fumaric acid and stirred for 2 days. The crystals were filtered off and dried. There was obtained 0.56 g (37.5%) of 2-(5-fluoro-3-methoxyindol-1-yl)-ethylamine fumarate (1:1) as beige crystals with a m.p. of 167°.

EXAMPLE 4 a) A solution of 1 g of 5-chloroindole in 30 ml of 1,2-dibromoethane was treated with 30 ml of 28% NaOH and 80 mg of tetrabutyl-ammonium bromide. The mixture was stirred at 50° for 3 hours. The phases were separated and the aqueous phase was extracted with toluene. The combined organic phases were washed with water and dried over sodium sulfate. The solvent was distilled off and the residue was chromatographed over 150 g of silica gel with hexane-ethyl acetate (5:1). There were obtained 1.17 g (69%) of 1-(2-bromoethyl)-5-chloroindole as white crystals with a m.p. of 71°.

b) A suspension of 0.55 g of 1-(2-bromoethyl)-5-chloroindole in 60 ml of liquid ammonia was stirred in an autoclave at 80° for 18 hours. After evaporation of the ammonia the residue was taken up in dichloromethane and washed with water and saturated sodium chloride solution. The organic phase was dried over sodium surfate and the solvent was distilled off. The residue was dissolved in 60 ml of ether and 3 ml of methanol and treated with 0.25 g of fumaric acid and stirred for 2 days. The crystals were filtered off and dried. There was obtained 0.51 g (88%) of 2-(5-chloroindol-1-yl)-ethylamine fumarate (1:0.7) as white crystals (m.p. 167°).

EXAMPLE 5 a) 400 ml of 50% potassium hydroxide solution were added dropwise at 2°–4° over a period of 90 min. to a solution of 145 ml (1.02 mol) of 2-methylacetoacetic ester in 1 l of ethanol. 2 l of ice-water were added and the mixture was treated rapidly with a diazonium salt solution which had been prepared as follows: 200 ml of a 25% hydrochloric acid solution were added dropwise while cooling with an ice bath to a solution of 145.6 g (1 mol) of 3-chloro-4-fluoroaniline in 1 l of ethanol. Subsequently, 137 ml (1.02 mol) of isopentyl nitrite were added at 4° within 90 min. The orange emulsion, which resulted from the addition of the diazonium salt solution, was poured into 4 l of water and extracted once with 4 l of toluene and twice with 2 l of toluene each time. The combined organic phases were dried over sodium sulfate, filtered and concentrated to a volume of 1.5 l. After boiling on a water separator for 30 minutes a solution of 203 g of p-toluenesulfonic acid monohydrate in 1.5 l of toluene was added and the mixture was heated on a water separator for a further hour. After cooling the mixture was extracted with 1.5 l of 1N hydrochloric acid, 1.5 l of 1N sodium hydroxide solution and 0.4 l of saturated sodium chloride solution. The aqueous phases were back-washed with 1.5 l of toluene and the combined organic phases were dried over sodium sulfate, filtered and evaporated. The residue was chromatographed over 3 kg of silica gel with toluene. 10.3 g (4.2%) of ethyl 6-chloro-5-fluoroindole-2-carboxylate were obtained. A sample was recrystallized from toluene and then showed a m.p. of 190°–191°. A second fraction contained 7 g (2.9%) of ethyl 4-chloro-5-fluoroindole-2-carboxylate as brown crystals with a m.p. of 179°–182°.

b) A suspension of 6.3 g of ethyl 4-chloro-5-fluoroindole-2-carboxylate in 260 ml of ethanol was treated with 130 ml of 2N sodium hydroxide solution and stirred for 3 hours. Ethanol was evaporated and the reaction solution was adjusted to pH 1 with 25% hydrochloric acid. The precipitate was washed with water and dried. There were obtained 5.3 g (96%) of crude 4-chloro-5-fluoroindole-2-carboxylic acid which was used in the next step without further purification.

c) A metal bath was heated to 300°–320°. 4.8 g of 4-chloro-5-fluoroindole-2-carboxylic acid were introduced under argon and, after three minutes, the metal bath was removed. The reaction mixture was distilled in a bulb-tube at 0.15 mbar and 75° bath temperature. There were obtained 3.15 g (83%) of 4-chloro-5-fluoroindole as white crystals with m.p. 41°–43°.

d) A solution of 130 mg of 4-chloro-5-fluoroindole in 3.7 ml of 1,2-dibromoethane was treated with 3.7 ml of 28% NaOH and 7.7 mg of tetrabutylammonium bromide. The mixture was stirred at 50° for 5 hours. The phases were separated and the aqueous phase was s extracted with toluene. The combined organic phases were washed with water and dried over sodium sulfate. The solvent was distilled off and the residue was chromatographed over 15 g of silica gel with hexane-ethyl acetate (5:1). There was obtained a yellow oil which was suspended in 30 ml of liquid ammonia and stirred in an autoclave at 80° for 16 hours. After evaporation of the ammonia the residue was taken up in dichloromethane and washed with water and saturated sodium chloride solution. The organic phase was dried over sodium sulfate and the solvent was distilled off. The residue was chromatographed over 15 g of silica gel with ethyl acetate-methanol (5:1). There were obtained 110 mg of a yellow oil which was dissolved in 16 ml of ether, treated with 60 mg (0.5 mmol) of fumaric acid and stirred for 2 days. The crystals were filtered off and dried. There were obtained 150 mg (59%) of 2-(4-chloro-5-fluoro-indol-1-yl)-ethylamine fumarate (1:1) with m.p. 200°–201° (dec.)

EXAMPLE 6 a) A suspension of 21.8 g of ethyl 6-chloro-5-fluoroindole-2as carboxylate in 450 ml of ethanol was treated with 180 ml of 2N sodium hydroxide solution and stirred for 21 hours. The solution was evaporated and the residue was taken up in 450 ml of water and treated with 60 ml of 25% hydrochloric acid. The precipitate was washed with water and dried. 18.8 g (97.7%) of 6-chloro-5-fluoroindole-2-carboxylic acid were obtained. A sample was recrystallized from toluene and then showed a m.p. of 274°–176°.

b) A metal bath was heated to 300°–320°. 6.4 g of 6-chloro-5-fluoroindole-2-carboxylic acid were introduced under argon and, after three minutes, the metal bath was removed. After cooling the reaction mixture was chromatographed over 25 g of silica gel with hexane-ethyl acetate (4:1). There were obtained 4.17 g (85%) of 6-chloro-5-fluoroindole as beige crystals. A sample was triturated with hexane and then showed a m.p. of 96–98°.

c) A solution of 0.95 g of 6-chloro-5-fluoroindole in 30 ml of 1,2-dibromoethane was treated with 30 ml of 28% NaOH and 60 mg of tetrabutylammonium bromide. The mixture was stirred for 8 hours. The phases were separated and the aqueous phase was extracted with toluene. The combined organic phases were washed with water and dried over sodium sulfate. The solvent was distilled off and the residue was chromatographed over 100 g of silica gel with hexane-ethyl acetate (6:1). There was obtained a light brown oil which was suspended in 120 ml of liquid ammonia and stirred in an autoclave at 80° for 16 hours. After evaporation of the ammonia the residue was taken up in dichloromethane and washed with water and saturated sodium chloride solution. The organic phase was dried over sodium sulfate and the solvent was distilled off. The residue was dissolved in 120 ml of ether and 6 ml of methanol, treated with 0.5 g of fumaric acid and stirred overnight. The crystals were filtered off and dried. There was obtained 1 g (61%) of 2-(6-chloro-5-fluoro-indol-1-yl)-ethylamine fumarate (1:0.7) with m.p. 192°–193° (dec.)

EXAMPLE 7 a) A solution of 1.76 g of ethyl 4-methyl-3-methoxyindole-2-carboxylate in 90 ml of ethanol was treated with 45 ml of 2N sodium hydroxide solution and stirred at room temperature for 17 hours. The alcohol was evaporated and the residue was treated with 60 ml o of 2N hydrochloric acid. The separated crystals were filtered off, washed with water and dried. There were obtained 1.2 g (78%) of 4-methyl-3-methoxyindole-2-carboxylic acid as brown crystals with m.p. 136°.

b) 1.2 g of 4-methyl-3-methoxyindole-2-carboxylic acid were heated at 150° until gas no longer evolved. There was obtained 0.94 g (quant.) of crude 4-methyl-3-methoxyindole which was used in the next step without further purification.

c) A solution of 0.94 g of 4-methyl-3-methoxyindole in 30 ml of 1,2-dibromoethane was treated with 30 ml of 28% NaOH and 400 mg of tetrabutylammonium bromide. The mixture was stirred at 40° for 24 hours. The reaction mixture was diluted with 150 ml of toluene and washed with 50 ml of water and 25 ml of saturated sodium chloride solution. The aqueous phases were back-extracted with 75 ml of toluene. The combined organic phases were dried with sodium sulfate. The solvent was distilled off and the residue was chromatographed over 70 g of silica gel with hexane-ethyl acetate (6:1). There was obtained a red oil which was suspended in 20 ml of liquid anunonia and stirred in an autoclave at 80° for 16 hours. After evaporation of the ammonia the residue was taken up in dichloromethane and washed with water and saturated sodium chloride solution. The organic phase was dried over sodium surfate and the solvent was distilled off. The residue was dissolved in 60 ml of ether and treated with 0.3 g of fumaric acid and stirred for 18 hours. The separated crystals were filtered off and dried. There was obtained 0.5 g (28%) of 2-(4-methyl-3-methoxy-indol-1-yl)-ethylamine fumarate (1:0.9) with m.p. 163°–164°.

EXAMPLE 8 a) A suspension of 0.4 g of sodium hydride dispersion in 60 ml of tetrahydrofuran was treated with 1.74 g of 5-chlor-oindole at 0° and stirred at this temperature for 1 hour. After the addition of 1.6 ml of (RS)-methyloxirane the reaction mixture was stirred at room temperature for 48 hours and subsequently treated with 11 ml of water. The mixture was diluted with 300 ml of ether, washed with 140 ml of water and with 70 ml of saturated sodium chloride solution and the organic phase was dried over sodium sulfate. After removal of the solvent the residue was chromatographed over 60 g of silica gel with toluene-ethyl acetate (19:1). There were obtained 2.1 g (87%) of (RS)-1-(5-chloro-indol-1-yl)-propan-2-ol as a yellow oil.

MS: m/e (% base peak): 209, 211 (M⁺, 28), 164 (100)

b) A solution of 2 g of (RS)-1-(5-chloro-indol-1-yl)-propan-2-ol in 50 ml of dichloromethane was treated with 5.4 ml of triethylamine and cooled to 0°. 1.5 ml of methanesulfonyl chloride were added dropwise to this solution and the reaction mixture was stirred for 1 hour. The mixture was diluted with 480 ml of ether. The mixture was washed with 120 ml of 1M sodium carbonate solution and 60 ml of saturated sodium chloride solution and the aqueous phase was back-extracted with 240 ml of ether. The combined organic s phases were dried over sodium sulfate and the solvent was removed. The residue was dissolved in 50 ml of dimethylformamide and, after the addition of 1.26 g of sodium azide, stirred at 60° for 7 hours. The mixture was diluted with 500 ml of ether and extracted twice with 240 ml of water each time and once with 60 ml of saturated sodium chloride solution. The aqueous phase was back-extracted with 240 ml of ether and the combined organic phases were dried over sodium sulfate. The solvent was removed and the residue was chromatographed over 46 g of silica gel with toluene. There were obtained 2 g (90%) of (RS)-1-(2-azido-propyl)-5-chloroindole as a colourless oil.

MS: m/e (% base peak): 234, 236 (M⁺, 20), 164 (100)

c) A suspension of 0.2 g of platinum oxide in 40 ml of ethanol was stirred under a hydrogen atmosphere for half an hour and subsequently treated with a solution of 1.9 g of (RS)-1-(2-azido-propyl)-5-chloroindole in 40 ml of ethanol. The reaction mixture was stirred at room temperature for two hours. The catalyst was filtered off and washed with ethanol. The solution was evaporated and the residue was dissolved in 160 ml of ether and treated with 0.94 g of fumaric acid and stirred overnight. The separated crystals were filtered off and dried. There were obtained 1.85 g (70%) of (RS)-2-(5-chloro-indol-1-yl)-1-methyl-ethylamine fumarate (1:1.9) as white crystals with m.p. 183°–185° (dec.)

EXAMPLE 9 a) A suspension of 0.55 g of sodium hydride dispersion in 75 ml of tetrahydrofuran was treated with 2 g of 5-fluoroindole at 0° and stirred at this temperature for 1 hour. After the addition of 2.1 ml of (RS)-methyloxirane the reaction mixture was stirred at room temperature for 24 hours and subsequently treated with 5 ml of water. The mixture was diluted with ether, washed three times with 75 ml of water each time and with 70 ml of saturated sodium chloride solution and the organic phase was dried over sodium sulfate. After removal of the solvent the residue was chromatographed over 60 g of silica gel with toluene-ethyl acetate (19:1). There were obtained 1.8 g (62%) of (RS)-1-(5-fluoro-indol-1-yl)-propan-2-ol as a yellow oil.

MS: m/e (% base peak): 193 (M⁺, 22), 148 (100)

b) A solution of 1.75 g of (RS)-1-(5-fluoro-indol-1-yl)-propan-2-ol in 45 ml of dichloromethane was treated with 3.8 ml of triethylamine and cooled to 0°. 1.4 ml of methanesulfonyl chloride as were added dropwise to this solution and the reaction nfixture was stirred for one hour. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 45 ml of dimethylformamide and, after the addition of 1.18 g of sodium azide, stirred at 60° for 6 hours. The mixture was diluted with ether and extracted with water and with 60 ml of saturated sodium chloride solution. The aqueous phase was back-extracted with ether and the combined organic phases were dried over sodium sulfate. The solvent was removed and the residue was chromatographed over 20 g of silica gel with toluene. There were obtained 1.8 g (91%) of (RS)-1-(2-azido-propyl)-5-fluoroindole as a colourless oil.

MS: m/e (% base peak): 218 (M⁺, 19), 148 (100)

c) A solution of 1.7 g of (RS)-1-(2-azido-propyl)-5-fluoroindole in 80 ml of ethanol was hydrogenated over 170 mg of Pd-C (5%). The catalyst was filtered off and washed with ethanol. The solution was evaporated and the residue was dissolved in 240 ml of ether and treated with 0.93 g of fumaric acid and stirred overnight. The separated crystals were filtered off and dried. There were obtained 2.3 g (95.8%) of (RS)-2-(5-fluoro-indol-1-yl)-1-methyl-ethylamine fumarate (1:1) as white crystals with m.p. 169°–170° (dec.)

EXAMPLE 10 a) A suspension of 0.75 g of sodium hydride dispersion in 100 ml of tetrahydrofuran was treated with 3.38 g of 6-chloro-5-fluoroindole at 0° and stirred at this temperature for 1 hour. After the addition of 2.8 ml of (RS)-methyloxirane the reaction mixture was stirred at room temperature for 48 hours and subsequently treated with 11 ml of water. The mixture was diluted with ether, washed with water and with saturated sodium chloride solution and the organic phase was dried over sodium sulfate. After removal of the solvent the residue was chromatographed over 75 g of silica gel with toluene-ethyl acetate (19:1). There were obtained 2.87 g (63%) of (RS)-1-6-chloro-5-fluoro-indol-1-yl)-propan-2-ol as beige crystals with m.p. 185°–186°.

b) A solution of 2.85 g of (RS)-1(6-chloro-5-fluoro-indol-1-yl)-propan-2-ol in 60 ml of dichloromethane was treated with 5.2 ml of triethylamine and cooled to 0% 1.9 ml of methanesulfonyl chloride were added dropwise to this solution and the reaction mixture was stirred for one hour. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 60 ml of dimethylformamide and, after the addition of 1.55 g of sodium azide, stirred at 60° for 3 hours. The mixture was diluted with ether and extracted twice with water and with saturated sodium chloride solution. The aqueous phase was back-extracted with ether and the combined organic phases were dried over sodium sulfate. The solvent was removed and the residue was chromatographed over 60 g of silica gel with toluene. There were obtained 2.87 g (92%) of (RS)-1-(2-azido-propyl)-6-chloro-5-fluoroindole as a yellowish oil.

MS: m/e (% base peak): 252,254 (M⁺, 20), 182 (100)

c) A suspension of 0.26 g of platinum oxide in 50 ml of ethanol was stirred under a hydrogen atmosphere for half an hour and subsequently treated with a solution of 2.8 g of (RS)-1-(2-azido-propyl)-6-chloro-5-fluoroindole in 50 ml of ethanol. The reaction mixture was stirred at room temperature for two hours. The catalyst was filtered off and washed with ethanol. The solution was evaporated and the residue was dissolved in 380 ml of ether and treated with 1.28 g of fumaric acid and stirred overnight. The separated crystals were filtered off and dried. There were obtained 3.6 g (95%) of (RS)-2o(6-chloro-5-fluoro-indol-1-yl)-1-methyl-ethylamine fumarate (1:1) as white crystals with m.p. 174°–175° (dec.)

EXAMPLE 11 a) A suspension of 0.26 g of sodium hydride dispersion in 35 ml of tetrahydrofuran was treated with 0.95 g of 5-fluoroindole at 0° and stirred at this temperature for 1 hour. After the addition of 1 ml of (S)-methyloxirane the reaction mixture was stirred at room temperature for 48 hours and subsequently treated with 7 ml of water. The mixture was diluted with 180 ml of ether, washed twice with 90 ml of water each time and with 50 ml of saturated sodium chloride solution and the organic phase was dried over sodium sulfate. After removal of the solvent the residue was chromatographed over 28 g of silica gel with toluene-ethyl acetate (19:1). There were obtained 1.15 g (84%) of (S)-1-(5-fluoro-indol-1-yl)-propan-2-ol as a light brown oil.

$[\alpha]^{20}_D = +48.4$ (c 0.25, CHCl$_3$)

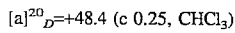

b) A solution of 1.1 g of (S)-1-(5-fluoro-indol-1-yl)-propan-2-ol in 30 ml of dichloromethane was treated with 3.17 ml of triethylamine and cooled to 0°. 0.88 ml of methanesulfonyl chloride was added dropwise to this solution and the reaction mixture was stirred for one hour. The mixture was diluted with 280 ml of ether. The mixture was washed twice with 70 ml of 1M sodium carbonate solution and 35 ml of saturated sodium chloride solution each time and the aqueous phase was back-extracted with 140 ml of ether. The combined organic phases were dried over sodium sulfate and the solvent was removed. The residue was dissolved in 30 ml of dimethylformamide and, after the addition of 0.74 g of sodium azide, stirred at 60° for 7 hours. The mixture was diluted with 280 ml of ether and extracted twice with 140 ml of water each time and once with 70 ml of saturated sodium chloride solution. The aqueous phase was back-extracted with 140 ml of ether and the combined organic phases were dried over sodium sulfate. The solvent was removed and the residue was chromatographed over 25 g of silica gel with toluene. There were obtained 1.14 g (95%) of (R)-1-(2-azido-propyl)-5-fluoroindole as a yellowish oil.

$[\alpha]^{20}_D = -124$ (c 0.25, CHCl$_3$)

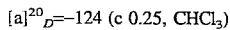

c) A suspension of 0.1 g of platinum oxide in 25 ml of ethanol was stirred under a hydrogen atmosphere for half an hour and subsequently treated with a solution of 0.92 g of (R)-1-(2-azido-propyl)-5-fluoroindole in 25 ml of ethanol. The reaction mixture was stirred at room temperature for two hours. The catalyst was filtered off and washed with ethanol. The solution was evaporated and the residue was dissolved in 150 ml of ether and treated with 0.58 g (5 mmol) of fumaric acid and stirred overnight. The separated crystals were filtered off and dried. There were obtained 1.14 g (88%) of (R)-2-(5-fluoro-indol-1-yl)-1-methyl-ethylamine fumarate (1:1) as white crystals with m.p. 159°–161° (dec.)

$[\alpha]^{20}_D = -38$ (c 0.25, CH$_3$OH)

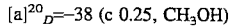

EXAMPLE 12 a) A suspension of 0.26 g of sodium hydride dispersion in 35 ml of tetrahydrofuran was treated with 0.95 g (7 mmol) of 5-fluoroindole at 0° and stirred at this temperature for 1 hour. After the addition of 1 ml of (R)-methyloxirane the reaction mixture was stirred at room temperature for 48 hours and subsequently treated with 7 ml of water. The mixture was diluted with 180 ml of ether, washed twice with 90 ml of water each time and with 50 ml of saturated sodium chloride solution and the organic phase was dried over sodium sulfate. After removal of the solvent the residue was chromatographed over 28 g of silica gel with toluene-ethyl acetate (19:1). There were obtained 1.09 g (80%) of (R)-1-(5-fluoro-indol-1-yl)-propan-2-ol as a light brown oil.

$[\alpha]^{20}_D = -48.8$ (c 0.2s, CHCl$_3$)

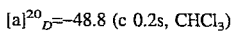

b) A solution of 1.04 g of (R)-1-(5-fluoro-indol-1-yl)-propan-2-ol in 30 ml of dichloromethane was treated with 3.17 ml of triethylamine and cooled to 0°. 0.88 ml of methanesulfonyl chloride was added dropwise to this solution and the reaction mixture was stirred for one hour. The mixture was diluted with 280 ml of ether. The mixture was washed twice with 70 ml of 1M sodium carbonate solution and 35 ml of saturated sodium chloride solution and the aqueous phase was back-extracted with 140 ml of ether. The combined organic phases were dried over sodium sulfate and the solvent was removed. The residue was dissolved in 30 ml of dimethylformamide and, after the addition of 0.74 g of sodium azide, stirred at 60° for 7 hours. The mixture was diluted with 280 ml of ether and extracted twice with 140 ml of water and once with 70 ml of saturated sodium chloride solution. The aqueous phase was back-extracted with 140 ml of ether and the combined organic phases were dried over sodium sulfate. The solvent was removed and the residue was chromatographed over 25 g of silica gel with toluene. There were obtained 1.14 g (97.4%) of (S)-1-(2-azido-propyl)-5-fluoroindole as a yellowish oil.

$[\alpha]^{20}_D = -119.2$ (c 0.25, CHCl$_3$)

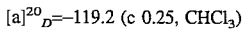

c) A suspension of 0.1 g of platinum oxide in 25 ml of ethanol was stirred under a hydrogen atmosphere for half an hour and subsequently treated with a solution of 1.12 g of (S)-1-(2-azido-propyl)-5-fluoroindole in 25 ml of ethanol. The reaction mixture was stirred at room temperature for two hours. The catalyst was filtered off and washed with ethanol. The solution was evaporated and the residue was dissolved in 150 ml of ether and treated with 0.58 g of fumaric acid and stirred overnight. The separated crystals were filtered off and dried. There were obtained 1.42 g (90%) of S)-2-(6-chloro-5-fluoro-indol-1-yl)-1-methylethylamine fumarate (1:1) as white crystals with m.p. 159°–161° (dec.)

$[\alpha]^{20}_D = -34$ (c 0.25, CH$_3$OH)

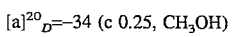

EXAMPLE 13 a) A suspension of 0.11 g of sodium hydride dispersion in 15 ml of tetrahydrofuran was treated with 0.5 g of 6-chloro-5-fluoroindole at 0° and stirred at this temperature for 1 hour. After the addition of 0.42 ml of (S)-methyloxirane the reaction mixture was stirred at room temperature for 85 hours and subsequently treated with water. The mixture was diluted with ether, washed with water and with saturated sodium chloride solution and the organic phase was dried over sodium sulfate. After removal of the solvent the residue was chromatographed over 25 g of silica gel with toluene-ethyl acetate (19:1). There was obtained 0.54 g (79%) of (S)-1-(6-chloro-5-fluoro-indol-1-yl)-propan-2-ol as beige crystals (m.p. 99°–101°).

b) A solution of 0.53 g of (S)-1-(6-chloro-5-fluoro-indol-1-yl)-propan-2-ol in 30 ml of dichloromethane was treated with 1 ml of triethylamine and cooled to 0°. 0.36 ml of methanesulfonyl chloride was added dropwise to this solution and the reaction mixture was stirred for one hour. The mixture was diluted with ether. The mixture was washed with 1M sodium carbonate solution and saturated sodium chloride solution and the aqueous phase was back-extracted extracted with ether. The combined organic phases were dried over sodium sulfate and the solvent was removed. The residue was dissolved in 10 ml of dimethylformamide and, after the addition of 0.3 g of sodium azide, stirred at 60° for 7 hours. The mixture was diluted with ether and extracted with water and with saturated sodium chloride solution. The aqueous phase was back-extracted with ether and the combined organic phases were dried over sodium sulfate. The solvent was removed and the residue was chromatographed over 20 g of silica gel with toluene-n-hexane (9:1). There was obtained 0.54 g (92%) of (R)-1-(2-azido-propyl)-6-chloro-5-fluoroindole as a yellowish oil.

$[a]^{20}_D = -131.6$ (c 0.25, CHCl$_3$)

c) A suspension of 0.05 g of platinum oxide in 10 ml of ethanol was stirred under a hydrogen atmosphere for half an hour and subsequently treated with a solution of 0.51 g of (R)-1-(2-azido-propyl)-6-chloro-5-fluoroindol in 10 ml of ethanol. The reaction mixture was stirred at room temperature for two hours. The catalyst was filtered off and washed with ethanol. The solution was evaporated and the residue was dissolved in 60 ml of ether and treated with 0.23 g of fumaric acid and stirred overnight. The separated crystals were filtered off and dried. There was obtained 0.55 g (69%) of (R)-2-(6-chloro-5-fluoro-indol-1-yl)-1-methyl-ethylamine fumarate (1:1.5) as white crystals with m.p. 153°–154° (dec.)

$[a]^{20}_D = -28.8$ (c 0.25, CH$_3$OH)

EXAMPLE 14 a) A suspension of 0.11 g of sodium hydride dispersion in 15 ml of tetrahydrofuran was treated with 0.5 g of 6-chloro-5-fluoroindole at 0° and stirred at this temperature for 1 hour. After the addition of 0.42 ml of (R)-methyloxirane the reaction mixture was stirred at room temperature for 85 hours and subsequently treated with is water. The mixture was diluted with ether, washed with water and with saturated sodium chloride solution and the organic phase was dried over sodium sulfate. After removal of the solvent the residue was chromatographed over 25 g of silica gel with toluene/ethyl acetate (19:1). There was obtained 0.51 g (74.6%) of (R)-1-(6-chloro-5-fluoro-indol-1-yl)-propan-2-ol as white crystals (m.p. 104°–105°.)

b) A solution of 0.28 g of (R)-1-(6-chloro-5-fluoro-indol-1-yl)-propan-2-ol in 6 ml of dichloromethane was treated with 0.5 ml of triethylamine and cooled to 0°. 0.2 ml of methanesulfonyl chloride was added dropwise to this solution and the reaction mixture was stirred for 1 hour. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 6 ml of dimethylformamide and, after the addition of 0.16 g of sodium azide, stirred at 60° for 7 hours. The mixture was diluted with ether and extracted with water and with saturated sodium chloride solution. The aqueous phase was back-extracted with ether and the combined organic phases were dried over sodium sulfate. The solvent was removed and the residue was chromatographed over 10 g of silica gel with toluene. There was obtained 0.29 g (93.5%) of (S)-1-(2-azido-propyl)-6-chloro-5-fluoroindole as a yellowish oil.

$[a]^{20}_D = +151.2$ (c 0.25, CHCl$_3$)

c) A suspension of 0.02 g of platinum oxide in 5 ml of ethanol was stirred under a hydrogen atmosphere for half an hour and subsequently treated with a solution of 0.26 g of (S)-1-(2-azido-propyl)-6-chloro-5-fluoroindole in 5 ml of ethanol. The reaction mixture was stirred at room temperature for two hours. The catalyst was filtered off and washed with ethanol. The solution was evaporated and the residue was dissolved in 30 ml of ether and treated with 0.12 g of fumaric acid and stirred overnight. The separated crystals were filtered off and dried. There was obtained 0.25 g (58.8%) of (S)-2-(6-chloro-5-fluoro-indol-1-yl)-1-methyl-ethylamine fumarate (1:1.6) as white crystals with m.p. 151°–152° (dec.)

$[a]^{20}_D = +31.6$ (c0.25, CH$_3$OH)

EXAMPLE 15 a) A suspension of 0.26 g of sodium hydride dispersion in 35 ml of tetrahydrofuran was treated with 0.95 g of 4-methylindole at 0° as and stirred at this temperature for 1 hour. After the addition of 1 ml of (RS)-methyloxirane the reaction mixture was stirred at room temperature for 48 hours and subsequently treated with water. The mixture was diluted with ether, washed with water and with saturated sodium chloride solution and the organic phase was dried over sodium sulfate. After removal of the solvent the residue was chromatographed over 25 g of silica gel with toluene-ethyl acetate (19:1). There was obtained 0.86 g (62.7%) of (RS)-1-(4-methyl-indol-1-yl)-propan-2-ol as a yellow oil.

MS: m/e (% base peak): 189 (M$^+$, 26), 144 (100)

b) A solution of 0.74 g of (RS)-1-(4-methyl-indol-1-yl)-propan-2-ol in 20 ml of dichloromethane was treated with 1.6 ml of triethylamine and cooled to 0°. 0.6 ml of methanesulfonyl chloride was added dropwise to this solution and the reaction mixture was stirred for 1 hour. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 20 ml of dimethylformamide and, after the addition of 0.5 g of sodium azide, stirred at 60° for 7 hours. The mixture was diluted with ether and extracted with water and saturated sodium chloride solution. The aqueous phase was back-extracted with ether and the combined organic phases were dried over sodium sulfate. The solvent was removed and the residue was chromatographed over 30 g of silica gel with toluene. There was obtained 0.68 g (81.2%) of (S)-1-(2-azido-propyl)-4-methylindole as an orange oil.

MS: m/e (% base peak): 214 (M$^+$, 20), 144 (100)

c) A solution of 0.67 g of (RS)-1-(2-azido-propyl)-4-methylindole in 30 ml of ethanol was hydrogenated over 70 mg of Pd-C (5%). The catalyst was filtered off and washed with ethanol. The solution was evaporated and the residue was dissolved in 90 ml of ether and treated with 0.35 g of fumaric acid and stirred overnight. The separated crystals were filtered off and dried. There was obtained 0.88 g (92.3%) of (RS)-2-(4-methyl-indol-1-yl)-1-methyl-ethylamine fumarate (1:1) as white crystals with m.p. 163°–164° (dec.)

EXAMPLE 16 a) A suspension of 0.56 g of sodium hydride dispersion in 75 ml of tetrahydrofuran was treated with 2.95 g of 5-bromoindole at 0° C. and stirred at this temperature for 1 hour. After the addition of 2.1 ml of (RS)-methyloxirane the reaction mixture was stirred at room temperature for 60 hours and subsequently treated with 15 ml of water. The mixture was diluted with 750 ml of ether, washed twice with 250 ml of water and with 125 ml of saturated sodium chloride solution and the organic phase was dried over sodium sulfate. After removal of the solvent the residue was chromatographed over 120 g of silica gel with toluene-ethyl acetate (19:1). There were obtained 3.4 g (89%) of (RS)-1-(5-bromo-indol-1-yl)-propan-2-ol as a yellow oil.

MS: m/e (% base peak): 253,255 (M$^+$, 41), 208,210 (100), 129 (70)

b) A solution of 3.36 g of (RS)-1-(5-bromo-indol-1-yl)-propan-2-ol in 60 ml of dichloromethane was treated with 7.37 ml of triethylamine and cooled to 0°. 2 ml of methanesulfonyl chloride were added dropwise to this solution and the reaction mixture was stirred for one hour. The mixture was diluted with 660 ml of ether. The mixture was washed twice with 135 ml of 1M sodium carbonate solution and 80 ml of saturated sodium chloride solution and the aqueous phase was back-extracted with 300 ml of ether. The combined organic phases were dried over sodium sulfate and the solvent was removed. The residue was dissolved in 60 ml of dimethylformamide and, after the addition of 1.72 g of sodium azide, stirred at 60° for 16 hours. The mixture was diluted with 660 ml of ether and extracted twice with 330 ml of water and once with 80 ml of saturated sodium chloride solution. The aqueous phase was back-extracted with 330 ml of ether and the combined organic phases were dried over sodium sulfate. The solvent was removed and the residue was chromatographed over 90 g of silica gel with toluene. There were obtained 3.22 g (87.2%) of (RS)-1-(2-azido-propyl)-5-bromoindole as a light yellow oil.

MS: m/e (% base peak): 278, 280 (M$^+$, 16), 208, 210 (87), 129 (100)

c) A suspension of 0.1 g of platinum oxide in 20 ml of ethanol was stirred under a hydrogen atmosphere for half an hour and subsequently treated with a solution of 1.12 g of (RS)-1-(2-azido-propyl)-5-bromoindole in 20 ml of ethanol and 2 ml of a 33% methylamine solution in ethanol. The reaction mixture was stirred at room temperature for 4 hours. The catalyst was filtered off and washed with ethanol. The solution was evaporated and the residue was dissolved in 120 ml of ether and 2.5 ml of methanol and treated with 0.46 g of fumaric acid and stirred overnight. The separated crystals were filtered off and dried. There were obtained 1.38 g (93%) of (RS)-2-(5-bromo-indol-1-yl)-1-methyl-ethylamine fumarate (1:1) as white crystals with m.p. 192°–193° (dec.)

EXAMPLE 17

A suspension of 0.28 g of sodium hydride dispersion in 40 ml of tetrahydrofuran was treated with 0.98 g of 6-methylindole at 0° and stirred at this temperature for 1 hour. After the addition of 1 ml of (RS)-methyloxirane the reaction mixture was stirred at room temperature for 60 hours and subsequently treated with 7 ml of water. The mixture was diluted with 370 ml of ether, washed twice with 120 ml of water and with 60 ml of saturated sodium chloride solution and the organic phase was dried over sodium sulfate. After removal of the solvent the residue was chromatographed over 35 g of silica gel with toluene-ethyl acetate (19:1). There was obtained 0.5 g (35%) of (RS)-1-(6-methyl-indol-1-yl)-propan-2-ol as light brown crystals with m.p. 65°–69°.

b) A solution of 0.49 g of (RS)-1-(6-methyl-indol-1-yl)-propan-2-ol in 10 ml of dichloromethane was treated with 1 ml of triethylamine and cooled to 0°. 0.5 ml of methanesulfonyl chloride was added dropwise to this solution and the reaction mixture was stirred for one hour. The mixture was diluted with ether. The mixture was washed twice with 1M sodium carbonate solution and saturated sodium chloride solution and the aqueous phase was back-extracted with ether. The combined organic phases were dried over sodium sulfate and the solvent was removed. The residue was dissolved in 20 ml of dimethylformamide and, after the addition of 0.5 g of sodium azide, stirred at 60° for 16 hours. The mixture was diluted with 660 ml of ether and extracted twice with water and once with 80 ml of saturated sodium chloride solution. The aqueous phase was back-extracted with ether and the combined organic phases were dried over sodium sulfate. The solvent was removed and the residue was chromatographed over 30 g of silica gel with toluene. There was obtained 0.5 g (90%) of (RS)-1-(2-azido-propyl)-5-methylindole as a light yellow oil.

c) A solution of 0.5 g of (RS)-1-(2-azido-propyl)-5-methylindole in 20 ml of ethanol was hydrogenated over 70 mg of Pd-C (5%). The catalyst was filtered off and washed with ethanol. The solution was evaporated and the residue was dissolved in 100 ml of ether and treated with 0.25 g of fumaric acid and stirred overnight. The separated crystals were filtered off and dried. There was obtained 0.43 g (60.5%) of (RS)-2-(6-methyl-indol-1-yl)-1-methyl-ethylamine fumarate as white crystals with m.p. 152°–153° (dec.)

EXAMPLE 18 a) A suspension of 0.26 g of sodium hydride dispersion in 35 ml of tetrahydrofuran was treated with 0.97 g of 6-fluoroindole at 0° and stirred at this temperature for 1 hour. After the addition of 1 ml of (RS)-methyloxirane the reaction mixture was stirred at room temperature for 48 hours and subsequently treated with 7 ml of water. The mixture was diluted with 180 ml of ether, washed twice with 90 ml of water and with 50 ml of saturated sodium chloride solution and the organic phase was dried over sodium sulfate. After removal of the solvent the residue was chromatographed over 28 g of silica gel with toluene-ethyl acetate (19:1). There were obtained 1.1 g (79.3%) of (RS)-1-(6-fluoro-indol-1-yl)-propan-2-ol as a colourless oil.

b) A solution of 1.1 g of (RS)-1-(6-fluoro-indol-1-yl)-propan-2-ol in 30 ml of dichloromethane was treated with 3.17 ml of triethylamine and cooled to 0°. 0.88 ml of methanesulfonyl chloride was added dropwise to this solution and the reaction mixture was stirred for 1 hour. The mixture was diluted with 280 ml of ether. The mixture was washed twice with 70 ml of 1M sodium carbonate solution and 35 ml of saturated sodium chloride solution and the aqueous phase was back-extracted with 140 ml of ether. The combined organic phases were dried over sodium sulfate and the solvent was removed. The residue was dissolved in 20 ml of dimethylformamide and, after the addition of 0.5 g of sodium azide, stirred at 60° for 7 hours. The mixture was diluted with 280 ml of ether and extracted twice with 140 ml of water and once with 70 ml of saturated sodium chloride solution. The aqueous phase was back-extracted with 140 ml of ether and the combined organic phases were dried over sodium sulfate. The solvent was removed and the residue was chromatographed over 25 g of silica gel with toluene. There was obtained 1 g (80.5%) of (RS)-1-(2-azido-propyl)-6-fluoroindole as a yellowish oil.

c) A solution of I g of (RS)-1-(2-azido-propyl)-6-fluoroindole in 30 ml of ethanol was hydrogenated over 100 mg of Pd-C (5%). The catalyst was filtered off and washed with ethanol. The solution was evaporated and the residue was dissolved in 100 ml of ether and treated with 0.5 g of fumaric acid and stirred overnight. The separated crystals were isolated and dried. There were obtained 1.1 g (78%) of (RS)-2-(6-fluoro-indol-1-yl)-1-methyl-ethylamine fumarate (1:1) as white crystals with m.p. 158°–159° (dec.)

EXAMPLE 19 a) 40 ml of 50% potassium hydroxide solution were added dropwise to a solution of 14.5 ml of 2-methylacetoacetic ester in 100 ml of ethanol at 2°–4°. 200 ml of ice-water were added and the mixture was treated with a diazonium salt solution which had been prepared as follows: 20 ml of a 25% hydrochloric acid solution were added dropwise while cooling with an ice bath to a solution of 10 ml of 3,4-difluoroaniline in 100 ml of ethanol. Subsequently, 13.7 ml of isopentyl nitrite were added at 4°. The emulsion which resulted from the addition of the diazonium salt solution was poured into water and extracted with toluene. The organic phase was dried over sodium sulfate, filtered and concentrated to a volume of 160 ml. A solution of 19 g of p-toluenesulfonic acid monohydrate was, after boiling on a water separator for 1 hour, added and the mixture was heated for a further hour. After cooling the mixture was extracted with 1N hydrochloric acid, 1N sodium hydroxide solution and saturated sodium chloride solution. The aqueous phases were backwashed with toluene and the combined organic phases were dried over sodium sulfate, filtered and evaporated. The residue was chromatographed over 170 g of silica gel with hexane-ethyl acetate (2:1). 8.9 g (39%) of crude ethyl 4,5-difluoroindole-2-carboxylate were obtained. A sample was recrystallized from hexane-ethyl acetate and then showed a m.p. of 149°–150°.

b) A solution of 2.06 g of ethyl 5,6-difluoroindole-2-carboxylate in 90 ml of ethanol was treated with 45 ml of 2N sodium hydroxide solution and stirred at room temperature for 17 hours. The alcohol was evaporated and the residue was treated with 50 ml of 2N hydrochloric acid. The separated crystals were filtered off, washed with water and dried. 1.78 g (98.8%) of 5,6-difluoroindole-2-carboxylic acid were obtained as brown crystals with m.p. 279°–280°.

c) A metal bath was heated to 330°. 1.74 g of 5,6-difluoroindole-2-carboxylic acid were introduced under argon. The black reaction residue was chromatographed over 60 g of silica gel with hexane-ethyl acetate (4:1). 1.11 g (82%) of 5,6-difluoroindole were obtained as pale brown crystals. A sample was sublimed and then showed a m.p. of 89°–91°.

d) A suspension of 0.12 g of sodium hydride dispersion in 15 ml of tetrahydrofuran was treated with 0.5 g of 5,6-difluoroindole at 0° and stirred at this temperature for 1 hour. After the addition of 0.46 ml of (R)-methyloxirane the reaction mixture was stirred at room temperature for 60 hours and subsequently treated with water. The mixture was diluted with ether, washed twice with water and with saturated sodium chloride solution and the organic phase was dried over sodium sulfate. After removal of the solvent the residue was chromatographed over 35 g of silica gel with toluene-ethyl acetate (19:1). 0.46 g (66.5%) of (R)-1-(5,6-difluoro-indol-1-yl)-propan-2-ol was obtained as yellowish crystals with m.p. 114°–116°.

$[\alpha]^{20}_D = -44.4$ (c 0.25, CHCl$_3$)

e) A solution of 0.43 g of (R)-1-(5,6-difluoro-indol-1-yl)-propan-2-ol in 10 ml of dichloromethane was treated with 0.86 ml of triethylamine and cooled to 0°. 0.32 ml of methanesulfonyl chloride was added dropwise to this solution and the reaction mixture was stirred for 1 hour. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 10 ml of dimethylformamide and, after the addition of 0.26 g of sodium azide, stirred at 60° for 7 hours. The mixture was diluted with ether and extracted twice with water and once with saturated sodium chloride solution. The aqueous phase was back-extracted with ether and the combined organic phases were dried over sodium sulfate. The solvent was removed and the residue was chromatographed over 15 g of silica gel with toluene. 0.4 g (83%) of (S)-1-(2-azido-propyl)-5,6-difluoroindole was obtained as a yellowish oil.

$[\alpha]^{20}_D = +97.2$ (c 0.25, CHCl$_3$)

f) A solution of 0.37 g of (S)-1-(2-azido-propyl)-5,6-difluoroindole in 15 ml of ethanol was hydrogenated over 40 mg of Pd-C (5%). The catalyst was filtered off and washed with ethanol. The solution was evaporated and the residue was dissolved in 50 ml of ether and treated with 0.17 g of fumaric acid and stirred overnight. The separated crystals were isolated and dried. 0.43 g (84%) of (S)-2-(5,6-difluoro-indol-1-yl)-1-methyl-ethylamine fumarate (1:1) was obtained as white crystals with m.p. 159°–160° (dec.)

$[\alpha]^{20}_D = +35.2$ (c 0.25, CH$_3$OH)

EXAMPLE 20 a) A suspension of 0.12 g of sodium hydride dispersion in 15 ml of tetrahydrofuran was treated with 0.5 g of 5,6-difluoroindole at 0° and stirred at this temperature for 1 hour. After the addition of 0.46 ml of (S)-methyloxirane the reaction mixture was stirred at room temperature for 60 hours and subsequently treated with water. The mixture was diluted with ether, washed twice with water and with saturated sodium chloride solution and the organic phase was dried over sodium sulfate. After removal of the solvent the residue was chromatographed over 35 g of silica gel with toluene-ethyl acetate (19:1). There was obtained 0.5 g (74%) of (S)-1-(5,6-difluoro-indol-1-yl)-propan-2-ol as yellowish crystals with m.p. 116°–118°.

$[\alpha]^{20}_D = +44.8$ (c 0.25, CHCl$_3$)

b) A solution of 0.48 g of (S)-1-(5,6-difluoro-indol-1-yl)-propan-2-ol in 10 ml of dichloromethane was treated with 0.97 ml of s triethylamine and cooled to 0°. 0.36 ml of methanesulfonyl chloride was added dropwise to this solution and the reaction mixture was stirred for 1 hour. The mixture was diluted with ether. The mixture was washed twice with 1M sodium carbonate solution and saturated sodium chloride solution and the aqueous phase was back-extracted with ether. The combined organic phases were dried over sodium sulfate and the solvent was removed. The residue was dissolved in 10 ml of dimethylformamide and, after the addition of 0.29 g of sodium azide, stirred at 60° for 7 hours. The mixture was diluted with ether and extracted twice with water and once with saturated sodium chloride solution. The aqueous phase was back-extracted with ether and the combined organic phases were dried over sodium sulfate. The solvent was removed and the residue was chromatographed over 15 g of silica gel with toluene. There was obtained 0.48 g (89.4%) of (R)- 1-(2-azido-propyl)-5,6-difluoroindole as a yellowish oil.

$[α]^{20}_D = -98$ (c 0.25, CHCl$_3$)

c) A solution of 0.45 g of (R)-1-(2-azido-propyl)-5,6difluoroindole in 20 ml of ethanol was hydrogenated over 40 mg of Pd-C (5%). The catalyst was filtered off and washed with ethanol. The solution was evaporated and the residue was dissolved in 50 ml of ether and treated with 0.21 g of fumaric acid and stirred overnight. The separated crystals were filtered off and dried. There was obtained 0.51 g (82%) of (R)-2-(S,6-difluoro-indol-1-yl)-1-methyl-ethylamine fumarate (1:1) as white crystals with m.p. 161°–162° (dec.)

$[α]^{20}_D = -34.4$ (c 0.25, CH$_3$OH)

EXAMPLE 21 a) 56 ml of 50% potassium hydroxide were added dropwise at 2°–4° to a solution of 20.3 ml of 2-methylacetoacetic ester in 140 ml of a s ethanol. 280 ml of ice-water were added and the mixture was treated rapidly with a diazonium salt solution which had been prepared as follows: 28 ml of a 25% hydrochloric acid solution were added dropwise while cooling with an ice bath to a solution of 25 g (140 mmol) of 4-fluoro-3-trifluoromethylaniline in 140 ml of ethanol. Subsequently, 19.2 ml of isopentyl nitrite were added at 4°. The emulsion which resulted from the addition of the diazonium salt solution was poured into water and extracted with toluene. The organic phase was dried over sodium sulfate, filtered and concentrated to a volume of 250 ml. After boiling on a water separator for 30 mins. a solution of 26.6 g of p-toluenesulfonic acid monohydrate in 250 ml of toluene was added and the mixture was heated for a further hour. After cooling the mixture was extracted with 1N hydrochloric acid, 1N sodium hydroxide solution and saturated sodium chloride solution. The aqueous phases were back-washed with toluene and the combined organic phases were dried over sodium surfate, filtered and evaporated. The residue was chromatographed over 200 g of silica gel with toluene. 3.2 g (6.3%) of crude ethyl 5-fluoro-6-trifluoromethylindole-2-carboxylate were obtained. A sample was triturated with hexane and then showed a m.p. of 159°–162°. A second fraction contained 1.4 g (3.6%) of ethyl 5-fluoro-4-trifluoromethylindole-2-carboxylate as orange crystals with a m.p. of 121°–124°.

b) A solution of 2.24 g of ethyl 5-fluoro-4-trifluoromethylindole-2-carboxylate in 80 ml of ethanol was treated with 40 ml of 2N sodium hydroxide solution and stirred at room temperature for 1 hour. The alcohol was evaporated and the solution was adjusted to pH 1 with 2N hydrochloric acid. The separated crystals were isolated, washed with water and dried. There were obtained 1.17 g (85%) of 5-fluoro-4-trifluoromethylindole-2-carboxylic acid as beige crystals with m.p. 204°–210°.

c) A suspension of 0.8 g of 5-fluoro-4-trifluoromethylindole-2-carboxylic acid in 16 ml of diphenyl ether was stirred at 260° for 4 hours and, after cooling to 0°, diluted with 16 ml of tetrahydrofuran. 122 mg of sodium hydride dispersion were added and the mixture was stirred for 1 hour. Subsequently, 0.46 ml of (S)-methyloxirane was added and the reaction mixture was stirred at room temperature for 60 hours. The mixture was extracted with diethyl ether, water and saturated sodium chloride solution and the organic phase was dried over sodium sulfate. The solvent was removed and the residue was chromatographed over 40 g of silica gel with hexane-toluene (1:1) and subsequently with toluene-ethyl acetate (15:1). There was obtained 0.3 g (35.5%) of (R)-1-(5-fluoro-4-trifluoromethyl-indol-1-yl)-propan-2-ol as light brown crystals.

$[α]^{20}_D = +34.4$ (c 0.25, CHCl$_3$)

d) A solution of 0.27 g of (R)-1-(5-fluoro-4-trifluoromethyl-indol-1-yl)-propan-2-ol in 5 ml of dichloromethane was treated with 0.44 ml of triethylamine and cooled to 0°. 0.16 ml of methanesulfonyl chloride was added dropwise to this solution and the reaction mixture was stirred for one hour. The mixture was diluted with ether. The mixture was washed twice with 1M sodium carbonate solution and saturated sodium chloride solution and the aqueous phase was back-extracted with ether. The combined organic phases were dried over sodium sulfate and the solvent was removed. The residue was dissolved in 5 ml of dimethylformamide and, after the addition of 0.13 g of sodium azide, stirred at 60° for 7 hours The mixture was diluted with ether and extracted twice with water and once with saturated sodium chloride solution. The aqueous phase was back-extracted with ether and the combined organic phases were dried over sodium sulfate. The solvent was removed and the residue was chromatographed over 10 g of silica gel with toluene-hexane (1:1). There was obtained 0.26 g (87.8%) of (S)-1-(2-azido-propyl)-5-fluoro-4-trifluoromethylindole as a colourless oil.

MS: m/e (% base peak): 286 (M+, 12), 216 (100)

e) A suspension of 26 mg of platinum oxide in 4.5 ml of ethanol was stirred under a hydrogen atmosphere for half an hour and subsequently treated with a solution of 0.26 g of (S)-1-(2-azido-propyl)-5-fluoro-4-trifluoromethylindole in 4.5 ml of ethanol. The reaction mixture was stirred at room temperature for 1 hour. The catalyst was filtered off and washed with ethanol. The solution was evaporated and the residue was dissolved in 27 ml of ether and 0.3 ml of methanol and treated with 105 mg of fumaric acid and stirred overnight. The separated crystals were isolated and dried. There was obtained 0.32 g (93.6%) of (S)-2-(5-fluoro-4-trifluoro-methylindol-1-yl)-1-methyl-ethylamine fumarate (1:1) as white crystals with m.p. 180°–181° (dec.)

$[α]^{20}_D = +36.8$ (c 0.25, CH$_3$OH)

EXAMPLE 22 a) A solution of 1.85 g of ethyl 5-fluoro-6-trifluoromethylindole-2-carboxylate in 60 ml of ethanol was treated with 30 ml of 2N sodium hydroxide solution and stirred at room temperature for 1 hour. The alcohol was evaporated and the solution was adjusted to pH 1 with 2N hydrochloric acid.

The separated crystals were isolated, washed with water and dried. There were obtained 1.5 g (90%) of 5-fluoro-6-trifluoromethylindole-2-carboxylic acid as brown crystals with m.p. 178°–180°.

b) A suspension of 0.75 g of 5-fluoro-6-trifluoromethylindole-2-carboxylic acid in 16 ml of diphenyl ether was stirred at 260° for 4 hours and, after cooling to 0°, diluted with 16 ml of tetrahydrofuran. 113 mg of sodium hydride dispersion were added and the mixture was stirred for 1 hour. Subsequently, 0.43 ml of (R)-methyloxirane was added and the reaction mixture was stirred at room temperature for 60 hours. The mixture was extracted with diethyl ether, water and saturated sodium chloride solution and the organic phase was dried over sodium sulfate. The solvent was removed and the residue was chromatographed over 40 g of silica gel with hexane-toluene (1:1) and subsequently with toluene-ethyl acetate (15:1). There was obtained 0.15 g (18.9%) of (R)-1-(5-fluoro-6-trifluoromethyl-indol-1-yl)-propan-2-ol as light brown crystals.

c) A solution of 0.15 g of (R)-1-(5-fluoro-6-trifluoromethyl-indol-1-yl)-propan-2-ol in 3 ml of dichloromethane was treated with 0.24 ml of triethylamine and cooled to 0°. 0.09 ml of methanesulfonyl chloride was added dropwise to this solution and the reaction mixture was stirred for 1 hour. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 3 ml of dimethylformamide and, after the addition of 0.07 g of sodium azide, stirred at 60° for 7 hours. The mixture was diluted with ether and extracted twice with water and once with saturated sodium chloride solution. The aqueous phase was back-extracted with ether and the combined organic phases were dried over sodium sulfate. The solvent was removed and the residue was chromatographed over 8 g of silica gel with toluene-hexane (1:1). There was obtained 0.13 g (79.2%) of (S)-1-(2-azido-propyl)-5-fluoro-6-trifluoromethylindole as a colourless oil.

MS: m/e (% base peak): 286 (M+, 12), 216 (100)

d) A suspension of 13 mg of platinum oxide in 2.5 ml of ethanol was stirred under a hydrogen atmosphere for half an hour and subsequently treated with a solution of 0.13 g of (S)-1-(2-azido-propyl)-5-fluoro-6-trifluoromethylindole in 2.5 ml of ethanol. The reaction mixture was stirred at room temperature for 1 hour. The catalyst was filtered off and washed with ethanol. The solution was evaporated and the residue was dissolved in 14 ml of ether and 0.1 ml of methanol and treated with 53 mg of fumaric acid and stirred overnight. The separated crystals were filtered off and dried. There was obtained 0.16 g (93.5%) of (S)-2-(5-fluoro-6-trifluoromethylindol-1-yl)-1-methyl-ethylamine fumarate (1:1) as white crystals with m.p. 170°–171° (dec.)

$[\alpha]^{20}_D$=+24 (c 0.25, $CH_3OH$)

EXAMPLE 23 a) A suspension of 0.11 g of sodium hydride dispersion in 15 ml of tetrahydrofuran was treated with 0.5 g of 4-chloro-5-fluoroindole at 0° and stirred at this temperature for 1 hour. After the addition of 0.4 ml of (R)-methyloxirane the reaction mixture was stirred at room temperature for 48 hours and subsequently treated with water. The mixture was diluted with ether, washed with water and with saturated sodium chloride solution and the organic phase was dried over sodium sulfate. After removal of the solvent the residue was chromatographed over 30 g of silica gel with toluene-ethyl acetate (33:1). There was obtained 0.5 g (74.5%) of (R)-1-(4-chloro-5-fluoro-indol-1-yl)-propan-2-ol as a yellow oil.

MS: m/e (% base peak: 227, 229 (M+, 32), 182, 184 (100)

b) A solution of 0.49 g of (R)-1-(4-chloro-5-fluoro-indol-1-yl)-propan-2-ol in 11 ml of dichloromethane was treated with 0.9 ml of triethylamine and cooled to 0°. 0.33 ml of methanesulfonyl chloride was added dropwise to this solution and the reaction mixture was stirred for one hour. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 8 ml of dimethylformamide and, after the addition of 0.22 g of sodium azide, stirred at 60° for 7 hours. The mixture was diluted with ether and extracted twice with water and once with saturated sodium chloride solution. The aqueous phase was back-extracted with ether and the combined organic phases were dried over sodium sulfate. The solvent was removed and the residue was chromatographed over 12 g of silica gel with toluene. There was obtained 0.4 g (73.5%) of (S)-1-(2-azido-propyl)-4-chloro-5-fluoroindole as a colourless oil.

MS: m/e (% base peak): 252, 254 (M+, 34), 182, 184 (100)

c) A suspension of 40 mg of platinum oxide in 8 ml of ethanol was stirred under a hydrogen atmosphere for half an hour and subsequently treated with a solution of 0.4 g of (S)-1-(2-azido-propyl)-4-chloro-5-fluoroindole in 8 ml of ethanol. The reaction mixture was stirred at room temperature for 1 hour. The catalyst was filtered off and washed with ethanol. The solution was evaporated and the residue was dissolved in 46 ml of ether and 0.3 ml of methanol and treated with 180 mg of fumaric acid and stirred overnight. The separated crystals were filtered off and dried. There was obtained 0.48 g (83.8%) of (S)-2-(4-chloro-5-fluoroindol-1-yl)-1-methyl-ethylamine fumarate (1:1) as white crystals with m.p. 183°–184° (dec.)

$[\alpha]^{20}_D$=+32.4 (c 0.25, $CH_3OH$)

EXAMPLE 24 a) A suspension of 0.11 g of sodium hydride dispersion in 15 ml of tetrahydrofuran was treated with 0.5 g of 4-chloro-5-fluoroindole at 0° and stirred at this temperature for 1 hour. After the addition of 0.4 ml of (S)-methyloxirane the reaction mixture was stirred at s room temperature for 48 hours and subsequently treated with water. The mixture was diluted with ether, washed with water and with saturated sodium chloride solution and the organic phase was dried over sodium sulfate. After removal of the solvent the residue was chromatographed over 30 g of silica gel with toluene-ethyl acetate (33:1). There was obtained 0.53 g (78.9%) of (S)-1-(4-chloro-5-fluoro-indol-1-yl)-propan-2-ol as a yellow oil.

MS: m/e (% base peak): 227, 229 (M+, 32), 182, 184 (100)

b) A solution of 0.52 g of (S)-1-(4-chloro-5-fluoro-indol-1-yl)-propan-2-ol in 11 ml of dichloromethane was treated with 0.97 ml of triethylamine and cooled to 0°. 0.36 ml of methanesulfonyl chloride was added dropwise to this solution and the reaction mixture was stirred for one hour. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 8 ml of dimethylformamide and, after the addition of 0.22 g of sodium azide, stirred at 60° for 7 hours. The mixture was diluted with ether and extracted twice with water and once with saturated sodium chloride solution. The aqueous phase was back-extracted with ether and the combined organic phases were dried over sodium sulfate. The solvent was removed and the residue was chromatographed over 12 g of silica gel with toluene. There was obtained 0.4 g (70%) of (R)-1-(2-azido-propyl)-4-chloro-5-fluoroindole as a colourless oil.

MS: m/e (% base peak): 252, 254 (M+, 34), 182, 184 (100)

c) A suspension of 40 mg of platinum oxide in 8 ml of ethanol was stirred under a hydrogen atmosphere for half an hour and subsequently treated with a solution of 0.4 g of (R)-1-(2-azido-propyl)-4-chloro-5-fluoroindole in 8 ml of ethanol. The reaction mixture was stirred at room temperature for 1 hour. The catalyst was filtered off and washed with ethanol. The solution was evaporated and the residue was dissolved in 46 ml of ether and 0.3 ml of methanol and treated with 180 ml of fumaric acid and stirred overnight. The separated crystals were filtered off and dried. There was obtained 0.48 g (83.8%) of (R)-2-(4-chloro-5-fluoroindol-1-yl)-1-methyl-ethylamine fumarate (1:1) as white crystals with m.p. 186°–187° (dec.)

$[\alpha]^{20}_D = -32.4$ (c 0.25, $CH_3OH$)

EXAMPLE 25 a) A suspension of 0.26 g of sodium hydride dispersion in 35 ml of tetrahydrofuran was treated with 0.95 g of 5-methylindole at 0° and stirred at this temperature for 1 hour. After the addition of 1 ml of (RS)-methyloxirane the reaction mixture was stirred at room temperature for 48 hours and subsequently treated with water. The mixture was diluted with ether, washed with water and with saturated sodium chloride solution and the organic phase was dried over sodium sulfate. After removal of the solvent the residue was chromatographed over 30 g of silica gel with toluene-ethyl acetate (19:1). There was obtained 0.86 g (62.7%) of (RS)-1-(5-methyl-indol-1-yl)-propan-2-ol as a yellow oil.

b) A solution of 0.86 g of (RS)-1-(5-methyl-indol-1-yl)-propan-2-ol in 20 ml of dichloromethane was treated with 1.6 ml of triethylamine and cooled to 0°. 0.6 ml of methanesulfonyl chloride was added dropwise to this solution and the reaction mixture was stirred for 1 hour. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 20 ml of dimethylformamide and, after the addition of 0.6 g of sodium azide, stirred at 60° for 7 hours. The mixture was diluted with ether and extracted with water and saturated sodium chloride solution. The aqueous phase was back-extracted with ether and the combined organic phases were dried over sodium sulfate. The solvent was removed and the residue was chromatographed over 30 g of silica gel with toluene. There was obtained 0.68g (71.6%) of (RS)-1-(2-azido-propyl)-5-methylindole as a yellow oil.

MS: m/e (% base peak): 214 (M+, 20), 144 (100)

c) A solution of 0.6 g of (RS)-1-(2-azido-propyl)-5-methylindole as in 20 ml of ethanol was hydrogenareal over 50 mg of Pd-C (5%). The catalyst was filtered off and washed with ethanol. The solution was evaporated and the residue was dissolved in 90 ml of ether and treated with 0.35 g of fumaric acid and stirred overnight. The separated crystals were isolated and dried. There was obtained 0.83 g (87%) of (RS)-2-(5-methyl-indol-1-yl)-1-methyl-ethylamine fumarate (1:1) as white crystals with m.p. 165°–167° (dec.)

EXAMPLE 26 a) While cooling with an ice bath 1.35 g of sodium were dissolved in 30 ml of methanol and subsequently a solution of 4.65 g of 3-chloro-4-fluorobenzaldehyde and 6.75 g of methyl azidoacetate in 10 ml of methanol were added within 20 min. The reaction mixture was stirred at room temperature for 3 hours and then neutralized with 2N HCl. The mixture was extracted with ethyl acetate, washed with water and saturated sodium chloride solution and the organic phase was dried over sodium sulfate. The solvent was removed and the residue was chromatographed over 250 g of silica gel with n-hexane-toluene 2:1. There were obtained 2.5 g (33%) of methyl 3-chloro-4-fluoro-a-azidocinnamate as yellow crystals with m.p. 72°–74°.

b) A mixture of 2.38 g of methyl 3-chloro-4-fluoro-a-azido-cinnamate and 180 ml of xylene was heated under reflux for 45 min. The solvent was removed. There were obtained 2.04 g (quant.) of an almost 1:1 mixture of methyl 5-chloro-6-fluoro-indole-2-carboxylate and methyl 7-chloro-6-fluoro-indole-2-carboxylate as light yellow crystals which was used in the next step without further purification.

c) A suspension of 2.04 g of an almost 1:1 mixture of methyl 5-chloro-6-fluoro-indole-2-carboxylate and methyl 7-chloro-6-fluoro-indole-2-carboxylate in 90 ml of ethanol and 45 ml of 2N sodium hydroxide solution was stirred at room temperature for 1 hour. The alcohol was evaporated and the residue was treated with 55 ml of 2N hydrochloric acid. The separated crystals were isolated, washed with water and dried. There were obtained 1.92 g (quant.) of an almost 1:1 mixture of 5-chloro-6-fluoro-indole-2-carboxylic acid and 7-chloro-6-fluoro-indole-2-carboxylic acid as yellow crystals.

d) A suspension of 1.92 g of an almost 1:1 mixture of 5-chloro-6-fluoro-indole-2-carboxylic acid and 7-chloro-6-fluoro-indole-2-carboxylic acid in 45 ml of diphenyl ether was stirred at 260° for 4 hours. The reaction mixture was chromatographed over 100 g of silica gel with hexane and hexane-toluene (3:1). There were obtained 0.6 g (39%) of 5-chloro-6-fluoroindole as light brown crystals with m.p. 88°–90° and 0.22 g (14%) of 7-chloro-6-fluoroindole as a dark brown oil.

e) A suspension of 128 mg of sodium hydride dispersion in 8 ml of tetrahydrofuran was treated with 0.5 7 g of 5-chloro-6-fluoroindole at 0° and stirred at this temperature for 1 hour. After the addition of 0.48 ml of (R)-methyloxirane the reaction mixture was stirred at room temperature for 48 hours and subsequently treated with water. The mixture was diluted with ether, washed with water and with saturated sodium chloride solution and the organic phase was dried over sodium sulfate. After removing the solvent the residue was chromatographed over 25 g of silica gel with toluene-ethyl acetate (19:1). There was obtained 0.59 g (77%) of (R)-1-(5-chloro-6-fluoro-indol-1-yl)-propan-2-ol as beige crystals with m.p. 108°–110°.

f) A solution of 0.S7 g of (R)-1-(5-chloro-6-fluoro-indol-1-yl)-propan-2-ol in 12 ml of dichloromethane was treated with 0.4 ml of triethylamine and cooled to 0°. 0.2 ml of methanesulfonyl chloride was added dropwise to this solution and the reaction mixture was stirred for one hour. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 12 ml of dimethylformamide and, after the addition of 0.32 g of sodium azide, stirred at 60° for 7 hours. The mixture was diluted with ether and extracted with water and saturated sodium chloride solution. The aqueous phase was back-extracted with ether and the combined organic phases were dried over sodium sulfate. The solvent was removed and the residue was chromatographed over 15 g of silica gel with toluene-n-hexane 3:1. There was obtained 0.58 g (92%) of (S)-1-(2-azido-propyl)-5-chloro-6-fluoroindole as a colourless oil.

MS: m/e (% base peak): 252, 254 (M$^+$, 10), 182, 184 (100)

g) A suspension of 57 mg of platinum oxide in 10 ml of ethanol was stirred under a hydrogen atmosphere for half an hour and subsequently treated with a solution of 0.57 g of (S)-1-(2-azido-propyl)-5-chloro-6-fluoroindole in 10 ml of ethanol. The reaction mixture was stirred at room temperature for 1 hour. The catalyst was filtered off and washed with ethanol. The solution was evaporated and the residue was dissolved in 70 ml of ether and 2 ml of methanol and treated with 262 mg of fumaric acid and stirred overnight. The separated crystals were isolated and dried. There was obtained 0.63 g (82%) of (S)-2-(5-chloro-6-fluoroindol-1-yl)-1-methyl-ethylamine fumarate (1:1) as white crystals with m.p. 159°–161° (dec.)

EXAMPLE 27 a) A suspension of 45 mg of sodium hydride dispersion in 10 ml of tetrahydrofuran was treated with 0.2 g of 7-chloro-6-fluoroindole at 0° and stirred at this temperature for 1 hour. After the addition of 0.17 ml of (RS)-methyloxirane the reaction mixture was stirred at room temperature for 4 days and subsequently treated with water. The mixture was diluted with ether, washed with water and with saturated sodium chloride solution and the organic phase was dried over sodium sulfate. After removal of the solvent the residue was chromatographed over 15 g of silica gel with toluene-ethyl acetate (19:1). There was obtained 0.21 g (77.8%) of (RS)-1-(7-chloro-6-fluoro-indol-1-yl)-propan-2-ol as white crystals with m.p. 85°–87°.

b) A solution of 0.2 g of (RS)-1-(7-chloro-6-fluoro-indol-1-yl)-propan-2-ol in 4.5 ml of dichloromethane was treated with 0.4 ml of methylamine and cooled to 0°. 0.14 ml of methanesulfonyl chloride was added dropwise to this solution and the reaction mixture was stirred for one hour. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 6 ml of dimethylformamide and, after the addition of 0.15 g of sodium azide, stirred at 60° for 7 hours. The mixture was diluted with ether and extracted with water and saturated sodium chloride solution. The aqueous phase was back-extracted with ether and the combined organic phases were dried over sodium sulfate. The solvent was removed and the residue was chromatographed over 10 g of silica gel with toluene-n-hexane 1:1. There was obtained 0.17 g (80%) of (RS)-1-(2-azido-propyl)-7-chloro-6-fluoroindole as a colourless oH.

c) A suspension of 17 mg of platinum oxide in 4 ml of ethanol was stirred under a hydrogen atmosphere for half an hour and subsequently treated with a solution of 0.16 g of (RS)-1-(2-azido-propyl)-7-chloro-6-fluoroindole in 4 ml of ethanol. The reaction mixture was stirred at room temperature for 1 hour. The catalyst was filtered off and washed with ethanol. The solution was evaporated and the residue was dissolved in 20 ml of ether and 0.2 ml of methanol and treated with 74 mg of fumaric acid and stirred overnight. The separated crystals were isolated and dried. There was obtained 0.19 g (86.5%) of (RS)-2-(7-chloro-6-fluoroindol-1-yl)-1-methyl-ethylamine fumarate (1:1) as white crystals with m.p. 187°–188° (dec.)

EXAMPLE 28 a) A suspension of 75 ml of sodium hydride dispersion in 15 ml of tetrahydrofuran was treated with 0.33 g of 5-chloro-2-methylindole at 0° and stirred at this temperature for 1 hour. After the addition of 0.28 ml of (RS)-methyloxirane the reaction mixture was stirred at room temperature for 48 hours and subsequently treated with water. The mixture was diluted with ether, washed with water and with saturated sodium chloride solution and the organic phase was dried over sodium sulfate. After removal of the solvent the residue was chromatographed over 13 g of silica gel with toluene-ethyl acetate (19:1). There was obtained 0.27 g (61.7%) of (RS)-1-(5-chloro-2-methyl-indol-1-yl)-propan-2-ol as a yellow oil.

MS: m/e (% base peak): 223, 225 (M$^+$, 26), 178, 180 (100)

b) A solution of 0.26 g of (RS)-1-(5-chloro-2-methyl-indol-1-yl)-propan-2-ol in 6 ml of dichloromethane was treated with 0.5 ml of triethylamine and cooled to 0°. 0.2 ml of methanesulfonyl chloride was added dropwise to this solution and the reaction mixture was stirred for one hour. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 6 ml of dimethylformamide and, after the addition of 0.15 g of sodium azide, stirred at 60° for 7 hours. The mixture was diluted with ether and extracted with water and saturated sodium chloride solution. The aqueous phase was back-extracted with ether and the combined organic phases were dried over sodium sulfate. The solvent was removed and the residue was chromatographed over 10 g of silica gel with toluene-n-hexane 1:1. There was obtained 0.17 g (58.6%) of (RS)-1-(5-chloro-2-methyl-indol-1-yl)-propan-2-ol as a colourless oil.

MS: m/e (% base peak): 223, 225 (M$^+$, 26), 178, 180 (100)

c) A suspension of 16 ml of platinum oxide in 4 ml of ethanol was stirred under a hydrogen atmosphere for half an hour and subsequently treated with a solution of 0.16 g of (RS)-1-(5-chloro-2-methyl-indol-1-yl)-propan-2-ol in 4 ml of ethanol. The reaction mixture was stirred at room temperature for 1 hour. The catalyst was filtered off and washed with ethanol. The solution was evaporated and the residue was dissolved in 20 ml of ether and 0.2 ml of methanol and treated with 74 ml of fumaric acid and stirred overnight. The separated crystals were isolated and dried. There was obtained 0.19 g (86.5%) of (RS)-2-(5-chloro-2-methylindol-1-yl)-1-methyl-ethylamine fumarate (1:1) as white crystals with m.p. 193°–194° (dec.)

EXAMPLE 29 a) A suspension of 263 mg of sodium hydride dispersion in 35 ml of tetrahydrofuran was treated with 0.94 g of 5-fluoroindole at 0° and stirred at this temperature for 1 hour. After the addition of 1.22 ml of (RS)-butylene oxide the reaction mixture was stirred at room temperature for 96 hours and subsequently treated with water. The mixture was diluted with ether, washed with water and with saturated sodium chloride solution and the organic phase was dried over sodium sulfate. After removal of the solvent the residue was chromatographed over 60 g of silica gel with toluene. There were obtained 1.2 g (83%) of (RS)-5-fluoro-indol-1-yl)-butan-2-ol as a yellow oil.

MS: m/e (% base peak): 207 ($M^+$, 22), 148 (100)

b) A solution of 1.15 g of (RS)-5-fluoro-indol-1-yl)-butan-2-ol in 28 ml of dichloromethane was treated with 3 ml of triethylamine and cooled to 0°. 0.86 ml of methanesulfonyl chloride was added dropwise to this solution and the reaction mixture was stirred for one hour. The mixture was diluted with ether. The mixture was as washed with 1M sodium carbonate solution and saturated sodium chloride solution and the aqueous phase was back-extracted with ether. The combined organic phases were dried over sodium sulfate and the solvent was removed. The residue was dissolved in 28 ml of dimethylformamide and, after the addition of 0.72 g of sodium azide, stirred at 60° for 15 hours. The mixture was diluted with ether and extracted with water and saturated sodium chloride solution. The aqueous phase was back-extracted with ether and the combined organic phases were dried over sodium sulfate. The solvent was removed and the residue was chromatographed over 34 g of silica gel with toluene. There were obtained 1.21 g (94%) of (RS)-1-(3-azido-butyl)-5-fluoroindole as a yellowish oil.

MS: m/e (% base peak): 232 ($M^+$, 14), 148 (100)

c) A solution of 1.18 g of (RS)-1-(3-azido-butyl)-5-fluoroindole in 25 ml of ethanol was hydrogenated over 120 mg of Pd-C (5%). The catalyst was filtered off and washed with ethanol. The solution was evaporated and the residue was dissolved in 1S0 ml of ether and 3 ml of methanol and treated with 0.47 g of fumaric acid and stirred overnight. The separated crystals were isolated and dried. There were obtained 1.26 g (77%) of (RS)-1-ethyl-2-(5-fluoroindol-1-yl)-ethylamine fumarate (1:1) as white crystals with m.p. 169°–171° (dec.)

EXAMPLE 30 a) 10 ml of 50% potassium hydroxide solution were added dropwise at 2°–4° over a period of 10 min. to a solution of 4.4 g of 2-propylacetoacetic ester in 26 ml of ethanol. 50 ml of ice-water were added and the mixture was treated rapidly with a diazonium salt solution which had been prepared as follows: 5 ml of a 25% hydrochloric acid solution were added dropwise while cooling with an ice bath to a solution of 2.4 ml of 4-fluoroaniline in 25 ml of ethanol. Subsequently, 3.4 ml of isopentyl nitrite were added at 4° within 10 min. The orange emulsion, which resulted from the addition of the diazonium salt solution, was poured into 100 ml of water and extracted once with 100 ml of toluene and twice with 50 ml of toluene each time. The combined organic phases were dried over sodium surfate, filtered and concentrated to a volume of 50 ml. After boiling on a water separator for 30 min. a solution of 7.13 g of p-toluenesulfonic acid monohydrate in 50 ml of toluene was added and the mixture was heated on a water separator for a further hour. After cooling the mixture was extracted with 50 ml of 1N hydrochloric acid, 50 ml of 1N sodium hydroxide solution and 25 ml of saturated sodium chloride solution. The aqueous phases were back-washed with 50 ml of toluene and the combined organic phases were dried over sodium sulfate, filtered and evaporated. The residue was chromatographed over 105 g of silica gel with toluene. 4.27 g (72.6%) of crude ethyl 3-ethyl-5-fluoroindole-2-carboxylate were obtained. A sample was recrystailized from hexane and then showed a m.p. of 111°–113°.

b) A suspension of 1.4 g of ethyl 3-ethyl-5-fluoroindole-2-carboxylate in 30 ml of ethanol was treated with 12 ml of 2N sodium hydroxide solution and stirred for 16 hours. Ethanol was evaporated and the reaction solution was adjusted to pH 1 with 25% hydrochloric acid. The precipitate was washed with water and dried. There were obtained 1.22 g (98%) of crude 4-chloro-5-fluoroindole-2-carboxylic acid which was used without further purification in the next step.

c) A suspension of 1.21 g of 3-ethyl-5-fluoroindole-2-carboxylic acid in 16 ml of diphenyl ether was stirred at 260° for 2 hours and, after cooling to 0°, diluted with 29 ml of tetrahydrofuran. 218 mg of sodium hydride dispersion were added and the mixture was stirred for one hour. Subsequently, 0.61 ml of (R)-methyloxirane was added and the reaction mixture was stirred at room temperature for 90 hours. The mixture was extracted with diethyl ether, water and saturated sodium chloride solution and the organic phase was dried over sodium sulfate. The solvent was removed and the residue was chromatographed over 120 g of silica gel with hexane-toluene (1:2) and subsequently with toluene-ethyl acetate (9:1). 0.8 g (62%) of (R)-1-(3-ethyl-5-fluoro-indol-1-yl)-propan-2-ol was obtained as pale brown crystals with m.p. 65°–67°.

d) A solution of 0.77 g of (R)-1-(3-ethyl-5-fluoro-indol-1-yl)-propan-2-ol in 17 ml of dichloromethane was treated with 1.9 ml of triethylamine and cooled to 0°. 0.54 ml of methanesulfonyl chloride was added dropwise to this solution and the reaction mixture was stirred for 2 hours. The mixture was diluted with ether. The mixture was washed with iM sodium carbonate solution and saturated sodium chloride solution and the aqueous phase was back-extracted with ether. The combined organic phases were dried over sodium sulfate and the solvent was removed. The residue was dissolved in 17 ml of dimethylformamide and, after the addition of 0.45 g of sodium azide, stirred at 60° overnight. The mixture was diluted with ether and extracted with water and saturated sodium chloride solution. The aqueous phase was back-extracted with ether and the combined organic phases were dried over sodium sulfate. The solvent was removed and the residue was chromatographed over 15 g of silica gel with toluene-hexane (2:1). 0.78 g (91%) of (S)-1-(2-azido-propyl)-3-ethyl-5-fluoroindole was obtained as a yellow oil.

MS: m/e (% base peak): 246 (M⁺, 20), 176 (100)

e) A suspension of 76 mg of platinum oxide in 15 ml of ethanol was stirred under a hydrogen atmosphere for half an hour and subsequently treated with a solution of 0.76 g of (S)-1-(2-azido-propyl)-3-ethyl-5-fluoroindole in 15 ml of ethanol. The reaction mixture was stirred at room temperature for 20 hours. The catalyst was filtered off and washed with ethanol. The solution was evaporated and the residue was dissolved in 90 ml of ether and 1.9 ml of methanol and treated with 358 mg of fumaric acid and stirred overnight. The separated crystals were isolated and dried. 0.91 g (88%) of (S)-2-(2-ethyl-5-fluoroindol-1-yl)-1-methyl-ethylamine fumarate (1:1) was obtained as white crystals with m.p. 164°–166° (dec.).

EXAMPLE 31 a) A suspension of 0.16 g of sodium hydride dispersion in 22 ml of tetrahydrofuran was treated with 0.38 g of 4-isopropyl-5-fluoroindole at 0° and stirred at this temperature for 1 hour. After the addition of 0.6 ml of (R)-methyloxirane the reaction mixture was stirred at room temperature for 120 hours and subsequently treated with water. The mixture was diluted with ether, washed with water and saturated sodium chloride solution and the organic phase was dried over sodium sulfate. After removal of the solvent the residue was chromatographed over 25 g of silica gel with toluene-ethyl acetate (19:1). 0.41 g (81%) of (R)-1-(4-isopropyl-5-fluoro-indol-1-yl)-propan-2-ol was obtained as a yellow oil.

MS: m/e (% base peak): 235 (M⁺, 32), 190 (100)

b) A solution of 0.41 g of (R)-1-(4-isopropyl-5-fluoro-indol-1-yl)-propan-2-ol in 10 ml of dichloromethane was treated with 0.74 ml of triethylamine and cooled to 0°. 0.27 ml of methanesulfonyl chloride was added dropwise to this solution and the reaction mixture was stirred for 2 hours. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 10 ml of dimethylformamide and, after the addition of 0.22 g of sodium azide, stirred at 60° overnight. The mixture was diluted with ether and extracted with water and saturated sodium chloride solution. The aqueous phase was back-extracted with ether and the combined organic phases were dried over sodium sulfate. The solvent was removed and 0.4 g (90%) of (S)-1-(2-azido-propyl)-4-isopropyl-5-fluoroindole was obtained as a yellow oil.

MS: m/e (% base peak): 260 (M⁺, 18), 190 (100)

c) A solution of 0.4 g of (S)-1-(2-azido-propyl)-4-isopropyl-5-fluoroindole in 15 ml of ethanol was hydrogenated over 40 mg of Pd-C (5%). The catalyst was filtered off and washed with ethanol. The solution was evaporated and the residue was dissolved in 45 ml of ether and 2 ml of methanol and treated with 0.17 g of fumaric acid and stirred overnight. The separated crystals were isolated and dried. 0.43 g (80%) of (S)-2-(4-isopropyl-5-fluoroindol-1-yl)-1-methyl-ethylamine fumarate (1:1) was obtained as white crystals with m.p. 166°–167° (dec.).

EXAMPLE 32 a) A suspension of 0.05 g of sodium hydride dispersion in 10 ml of tetrahydrofuran was treated with 0.23 g of 6-isopropyl-5-fluoroindole at 0° and stirred at this temperature for 1 hour. After the addition of 0.18 ml of (R)-methyloxirane the reaction mixture was stirred at room temperature for 70 hours and subsequently treated with water. The mixture was diluted with ether, washed with water and with saturated sodium chloride solution and the organic phase was dried over sodium sulfate. After removal of the solvent the residue was chromatographed over 15 g of silica gel with toluene-ethyl acetate (19:1). 0.08 g (27%) of (R)-1-(6-isopropyl-5-fluoro-indol-1-yl)-propan-2-ol was obtained as a yellow oil.

MS: m/e (% base peak): 235 (M⁺, 46), 190 (100)

b) A solution of 0.08 g of (R)-1-(6-isopropyl-5-fluoro-indol-1-yl)-propan-2-ol in 1.7 ml of dichloromethane was treated with 0.14 ml of triethylamine and cooled to 0°. 0.05 ml of methanesulfonyl chloride was added dropwise to this solution and the reaction mixture was stirred for 2 hours. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 1.7 ml of dimethylformamide and, after the addition of 0.04 g of sodium azide, stirred at 60° overnight. The mixture was diluted with ether and extracted with water and saturated sodium chloride solution. The aqueous phase was back-extracted with ether and the combined organic phases were dried over sodium sulfate. The solvent was removed and the residue was chromatographed over 10 g of silica gel with toluene-hexane (1:1). 0.06 g (75%) of (S)-1-(2-azido-propyl)-6-isopropyl-5-fluoroindole was obtained as a colourless oil.

MS: m/e (% base peak): 260 (M⁺, 22), 190 (100)

c) A solution of 0.05 g of (S)-1-(2-azido-propyl)-6-isopropyl-5-fluoroindole in 2 ml of ethanol was hydrogenated over 5 mg of Pd-C (5%). The catalyst was filtered off and washed with ethanol. The solution was evaporated and the residue was dissolved in 6 ml of ether and treated with 0.02 g of fumaric acid and stirred overnight. The separated crystals were isolated and dried. 0.07 g (97%) of (S)-2-(6-isopropyl-5-fluoroindol-1-yl)-1-methyl-ethylamine fumarate (1:1.2) was obtained as while crystals with m.p. 168°–169° (dec.).

EXAMPLE 33 a) A suspension of 1.16 g of 6-chloro-5-fluoro-3-ethyl-indole-2-carboxylic acid in 16 ml of diphenyl ether was stirred at 260° for 4 hours and, after cooling to 0°, diluted with 24 ml of tetrahydrofuran. 180 mg of sodium hydride dispersion were added and the mixture was stirred for one hour. Subsequently, 0.5 ml of (R)-methyloxirane was added and the reaction mixture was stirred at room temperature for 112 hours. The mixture was extracted with diethyl ether, water and saturated sodium chloride solution and the organic phase was dried over sodium sulfate. The solvent was removed and the residue was chromatographed over 120 g of silica gel with hexane-toluene (1:2) and subsequently with toluene-ethyl acetate (9:1). 0.97 g (79%) of (R)-1-(6-chloro-5-fluoro-3-ethylindol-1-yl)-propan-2-ol was obtained as pale brown crystals with m.p. 112°–114°.

b) A solution of 0.93 g of (R)-1-(6-chloro-5-fluoro-3-ethylindol-1-yl)-propan-2-ol in 18 ml of dichloromethane was treated with 2 of triethylamine and cooled to 0°. 0.57 ml of methanesulfonyl chloride was added dropwise to this solution and the reaction mixture was stirred for 2 hours. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 18 ml of dimethylformamide and, after the addition of 0.47 g of sodium azide, stirred at 60° overnight. The mixture was diluted with ether and extracted with water and saturated sodium chloride solution. The aqueous phase was back-extracted with ether and the combined organic phases were dried over sodium sulfate. The solvent was removed and the residue was chromatographed over 20 g of silica gel with toluene-hexane (2:1). 1 g (97%) of (S)-1-(2-azido-propyl)-6-chloro-5-fluoro-3-ethylindole was obtained as a yellow oil.

MS: m/e (% base peak): 280 (M$^+$, 20), 210 (100)

c) A suspension of 100 mg of platinum oxide in 17 ml of ethanol was stirred under a hydrogen atmosphere for half an hour and subsequently treated with a solution of 0.97 g of (S)-1-(2-azido-propyl)-6-chloro-5-fluoro-3-ethylindole in 17 ml of ethanol. The reaction mixture was stirred at room temperature for 15 hours. The catalyst was filtered off and washed with ethanol. The solution was evaporated and the residue was dissolved in 100 ml of ether and 2 ml of methanol and treated with 400 mg of fumaric acid and stirred overnight. The separated crystals were isolated and dried. 1.18 g (92%) of (S)-2-(6-chloro-5-fluoro-3-ethylindol-1-yl)-1-methyl-ethylamine fumarate (1:1) were obtained as white crystals with m.p. 172°–173° (dec.).

EXAMPLE 34 a) A suspension of 1.2 g of 4-chloro-5-fluoro-3-ethyl-indole-2-carboxylic acid in 16 ml of diphenyl ether was stirred at 260° for 4 hours and, after cooling to 0°, diluted with 24 ml of tetrahydrofuran. 186 mg of sodium hydride dispersion were added and the mixture was stirred for one hour. Subsequently, 0.5 ml of (R)-methyloxirane was added and the reaction mixture was stirred at room temperature for 114 hours. The mixture was extracted with diethyl ether, water and saturated sodium chloride solution and the organic phase was dried over sodium surfate. The solvent was removed and the residue was chromatographed over 120 g of silica gel with hexane-toluene (1:2) and subsequently with toluene-ethyl acetate (9:!). 102 g (80%) of (R)-1-(4-chloro-5-fluoro-3-ethylindol-1-yl)-propan-2-ol were obtained as pale brown crystals with m.p. 87°–88°.

b) A solution of 0.98 g of (R)-1-(4-chloro-5-fluoro-3-ethylindol-1-yl)-propan-2-ol in 19 ml of dichloromethane was treated with 2 ml of triethylamine and cooled to 0°. 0.6 ml of methanesulfonyl chloride was added dropwise to this solution and the reaction mixture was stirred for 2 hours. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 19 ml of dimethylformamide and, after the addition of 0.5 g of sodium azide, stirred at 60° overnight. The mixture was diluted with ether and extracted with water and saturated sodium chloride solution. The aqueous phase was back-extracted with ether and the combined organic phases were dried over sodium sulfate. The solvent was removed and the residue was chromatographed over 20 g of silica gel with toluene-hexane (2:1). 1.04 g (96%) of (S)-1-(2-azido-propyl)-4-chloro-5-fluoro-3-ethylindole were obtained as a yellow oil.

MS: m/e (% base peak): 280 (M$^+$, 26), 210 (100)

c) A suspension of 100 mg of platinum oxide in 18 ml of ethanol was stirred under a hydrogen atmosphere for half an hour and subsequently treated with a solution of 1.02 g of (S)-1-(2-azido-propyl)-4-chloro-5-fluoro-3-ethylindole in 18 ml of ethanol. The reaction mixture was stirred at room temperature for 4 hours. The catalyst was filtered off and washed with ethanol. The solution was evaporated and the residue was dissolved in 100 ml of ether and 2 ml of methanol and treated with 416 mg of fumaric acid and stirred overnight. The separated crystals were isolated and dried. 1.23 g (91%) of (S)-2-(4-chloro-5-fluoro-3-ethylindol-1-yl)-1-methyl-ethylamine fumarate (1:1) were obtained as white crystals with m.p. 178°–181° (dec.).

EXAMPLE 35 a) A suspension of 1.16 g of 5-fluoro-3-methyl-indole-2-carboxylic acid in 16 ml of diphenyl ether was stirred at 260° for 5 hours and, after cooling to 0°, diluted with 30 ml of tetrahydrofuran. 225 mg of sodium hydride dispersion were added and the mixture was stirred for one hour. Subsequently, 0.63 ml of (R)-methyloxirane was added and the reaction mixture was stirred at room temperature for 90 hours. The mixture was extracted with diethyl ether, water and saturated sodium chloride solution and the organic phase was dried over sodium surfate. The solvent was removed and the residue was chromatographed over 120 g of silica gel with hexane-toluene (1:1) and subsequently with toluene-ethyl acetate (19:1). 0.87 g (70%) of (R)-1-(5-fluoro-3-methylindol-1-yl)-propan-2-ol was obtained as a pale brown oil.

MS: m/e (% base peak): 207 (M$^+$, 22), 207 (100)

b) A solution of 0.84 g of (R)-1-(5-fluoro-3-methylindol-1-yl)-propan-2-ol in 20 ml of dichloromethane was treated with 2 ml of triethylamine and cooled to 0°. 0.63 ml of methanesulfonyl chloride was added dropwise to this solution and the reaction mixture was stirred for 2 hours. The mixure was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 20 ml of dimethylformamide and, after the addition of 0.52 g of sodium azide, stirred at 60° overnight. The mixture was diluted with ether and extracted with water and saturated sodium chloride solution. The aqueous phase was back-extracted with ether and the combined organic phases were dried over sodium sulfate. The solvent was removed and the residue was chromatographed over 90 g of silica gel with toluene-hexane (1:1). 0.87 g (90%) of (S)-1-(2-azido-propyl)-5-fluoro-3-methylindole was obtained as a colourless oil.

MS: m/e (% base peak): 280 (M$^+$, 26), 210 (100)

c) A solution of 0.85 g of (S)-1-(2-azido-propyl)-5-fluoro-3-methylindole in 37 ml of ethanol was hydrogenated over 85 mg of Pd-C (5%). The catalyst was filtered off and washed with ethanol. The solution was evaporated and the residue was dissolved in 100 ml of ether and 5 ml of methanol and treated with 0.42 g of fumaric acid and stirred overnight. The separated crystals were isolated and dried. 1.02 g (86%) of (S)-1-methyl-2-(5-fluoro-3-methylindol-1-yl)-ethylamine fumarate (1:1) were obtained as white crystals with m.p. 167°–168° (dec.).

EXAMPLE 36 a) A suspension of 0.07 g of sodium hydride dispersion in 10 ml of tetrahydrofuran was treated with 0.33 g of 6-chloro-5-fluoro-3-methylindole at 0° and stirred as this temperature for 1 hour. After the addition of 0.19 ml of (R)-methyloxirane the reaction mixture was stirred at room temperature for 17 hours and subsequently treated with water. The mixture was diluted with ether, washed with water and with saturated sodium chloride solution and the organic phase was dried over sodium sulfate. After removal of the solvent the residue was chromatographed over 20 g of silica gel with toluene-ethyl acetate (9:1). 0.22 g (50%) of (R)-1-(6-chloro-5-fluoro-3-methylindol-1-yl)-propan-2-ol was obtained as a yellow oil.

MS: m/e (% base peak): 241 ($M^+$, 28), 196 (100)

b) A solution of 0.2 g of (R)-1-(6-chloro-5-fluoro-3-methylindol-1-yl)-propan-2-ol in 4 ml of dichloromethane was treated with 0.47 mg of triethylamine and cooled to 0°. 0.13 ml of methanesulfonyl chloride was added dropwise to this solution and the reaction mixture was stirred for 5 hours. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 4 ml of dimethylformamide and, after the addition of 0.1 g of sodium azide, stirred at 60° overnight. The mixture was diluted with ether and extracted with water and saturated sodium chloride solution. The aqueous phase was back-extracted with ether and the combined organic phases were dried over sodium sulfate. The solvent was removed and the residue was chromatographed over 4.5 g of silica gel with toluene-hexane (2:1). 0.2 g (93%) of (S)-1-(2-azido-propyl)-6-chloro-5-fluoro-3-methylindole was obtained as a colourless oil.

MS: m/e (% base peak): 266 ($M^+$, 20), 296 (100)

c) A suspension of 20 mg of platinum oxide in 3.6 ml of ethanol was stirred under a hydrogen atmosphere for half an hour and subsequently treated with a solution of 0.19 g of (S)-1-(2-azido-propyl)-6-chloro-5-fluoro-3-methylindole in 3.6 ml of ethanol. The reaction mixture was stirred at room temperature for 17 hours. The catalyst was filtered off and washed with ethanol. The solution was evaporated and the residue was dissolved in 20 ml of ether and 0.4 ml of methanol and treated with 76 mg of fumaric acid and stirred overnight. The separated crystals were isolated and dried. 0.18 g (74%) of (S)-2-(6-chloro-5-fluoro-3-methylindol-1-yl)-1-methyl-ethylamine fumarate (1:1) was obtained as white crystals with m.p. 174°–176° (dec.).

EXAMPLE 37 a) A suspension of 1.98 g of 5-fluoro-3-methoxy-4-methylindole-2-carboxylic acid in 16 ml of diphenyl ether was stirred at 260° for 0.5 hour and, after cooling to 0°, diluted with 44 ml of tetrahydrofuran. 0.33 g of sodium hydride dispersion was added and the mixture was stirred for one hour. Subsequently, 1 ml of (R)-methyloxirane was added and the reaction mixture was stirred at room temperature for 90 hours. The mixture was extracted with diethyl ether, water and saturated sodium chloride solution and the organic phase was dried over sodium surfate. The solvent was removed and the residue was chromatographed over 120 g of silica gel with toluene and toluene-ethyl acetate (9:1). 1.69 g (80%) of (R)-1-(5-fluoro-3-methoxy-4-methylindol-1-yl)-propan-2-ol were obtained as a pale brown oil.

MS: m/e (% base peak): 237 ($M^+$, 56), 192 (100)

b) A solution of 1.64 g of (R)-1-(5-fluoro-3-methoxy-4-methylindol-1-yl)-propan-2-ol in 35 ml of dichloromethane was treated with 3.85 ml of triethylamine and cooled to 0°. 1.07 ml of methanesulfonyl chloride were added dropwise to this solution and the reaction mixture was stirred for 2 hours. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 30 ml of dimethylformamide and, after the addition of 0.82 g of sodium azide, stirred at 60° for 3 hours. The mixture was diluted with ether and extracted with water and saturated sodium chloride solution. The aqueous phase was back-extracted with ether and the combined organic phases were dried over sodium sulfate. The solvent was removed and the residue was chromatographed over 50 g of silica gel with toluene. 1.82 g (77%) of (77 %) (S)-1-(2-azido-propyl)-5-fluoro-3-methoxy-4-methylindole were obtained as a yellow oil.

MS: m/e (% base peak): 262 ($M^+$, 18), 192 (100)

c) A suspension of 127 mg of platinum oxide in 24 ml of ethanol was stirred under a hydrogen atmosphere for half an hour and subsequently treated with a solution of 1.27 g of (S)-1-(2-azido-propyl)-5-fluoro-3-methoxy-4-methylindole in 3.6 ml of ethanol. The reaction mixture was stirred at room temperature for 15 hours. The catalyst was filtered off and washed with ethanol. The solution was evaporated and the residue was dissolved in 145 ml of ether and 3 ml of methanol and treated with 0.56 g of fumaric acid and stirred overnight. The separated crystals were isolated and dried. 1.5 g (88%) of (S)-2-(5-fluoro-3-methoxy-4-methylindol-1-yl)-1-methyl-ethylamine fumarate (1:1) were obtained as white crystals with m.p. 173°–176° (dec.).

EXAMPLE 38 a) 1.4 g of 3-methoxy-4-methylindole-2-carboxylic acid were heated to 160° for 5 min. while gassing with argon and, after cooling to 0°, diluted with 34 ml of tetrahydrofuran. 0.25 g of sodium hydride dispersion was added and the mixture was stirred for one hour. Subsequently, 0.7 ml of (R)-methyloxirane was added and the reaction mixture was stirred at room temperature for 60 hours. The mixture was extracted with diethyl ether, water and saturated sodium chloride solution and the organic phase was dried over sodium sulfate. The solvent was removed and the residue was chromatographed over 60 g of silica gel with toluene-ethyl acetate (9:1). 0.8 g (54%) of (R)-1-(5-fluoro-3-methoxy-4-methylindol-1-yl)-propan-2-ol was obtained as a pale brown oil.

b) A solution of 0.8 g of (R)-1-(5-fluoro-3-methoxy-4-methylindol-1-yl)-propan-2-ol in 18 ml of dichloromethane was treated with 2 ml of triethylamine and cooled to 0°. 0.5 ml of methanesulfonyl chloride was added dropwise to this solution and the reaction mixture was stirred for 1 hour. The mixture was diluted with ether. The mixture was washed with 1M sodium carbonate solution and saturated sodium chloride solution and the aqueous phase was back-extracted with ether. The combined organic phases were dried over sodium sulfate and the solvent was removed. The residue was dissolved in 18 ml of dimethylformamide and, after the addition of 0.43 g of sodium azide, stirred at 60° for 3 hours. The mixture was diluted with ether and extracted with water and saturated sodium chloride solution. The aqueous phase was back-extracted with ether and the combined organic phases were dried over sodium sulfate. The solvent was removed and the residue was chromatographed over 22 g of silica gel with toluene-hexane (1:1). 0.46 g (57%) of (S)-1-(2-azido-propyl)-3-methoxy-4-methylindole was obtained as a yellow oil.

MS: m/e (% base peak): 244 (M⁺, 16), 174 (100)

c) A suspension of 45 mg of platinum oxide in 9 ml of ethanol was stirred under a hydrogen atmosphere for half an hour and subsequently treated with a solution of 0.45 g of (S)-1-(2-azido-propyl)-3-methoxy-4-methylindole in 9 ml of ethanol. The reaction mixture was stirred at room temperature for 3 hours. The catalyst was filtered off and washed with ethanol. The solution was evaporated and the residue was dissolved in 55 ml of ether and 1 ml of methanol and treated with 214 mg of fumaric acid and stirred overnight. The separated crystals were isolated and dried. 0.53 g (86%) of (S)-2-(3-methoxy-4-methylindol-1-yl)-1-methyl-ethylamine fumarate (1:1) was obtained as pale yellow crystals with m.p. 161°–162° (dec.).

EXAMPLE A

Tablets of the following composition were manufactured in the usual manner:

|  | mg/tablet |
| --- | --- |
| Active ingredient | 100 |
| Powd. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are manufactured in the usual manner:

|  | mg/tablet |
| --- | --- |
| Active ingredient | 200 |
| Powd. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are manufactured:

|  | mg/capsule |
| --- | --- |
| Active ingredient | 50 |
| Cryst. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The finished mixture is filled into hard gelatine capsules of suitable size.

I claim:

1. A compound of the formula

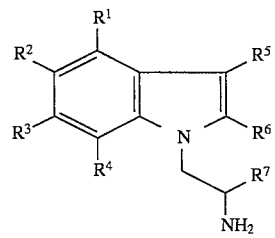

wherein $R^1$ to $R^4$ are, independently, hydrogen, halogen, lower-alkyl, cycloalkyl or trifluoromethyl, $R^5$ and $R^6$ are, independently, hydrogen, halogen, lower-alkyl, cycloalkyl, trifluoromethyl, hydroxy or lower-alkoxy and $R^7$ is lower-alkyl, or a pharmaceutically acceptable acid addition salt thereof.

2. A compound according to claim 1, wherein $R^7$ is methyl.

3. A compound according to claim 1, wherein $R^5$ and $R^6$ are hydrogen.

4. A compound according to claim 3, wherein $R^1$ is hydrogen or methyl, $R^2$ is hydrogen or fluorine, $R^3$ is hydrogen or chlorine and $R^4$ is hydrogen.

5. A compound selected from the group consisting of
(RS)-2-(5-Chloro-indol-1-yl)-1-methyl-ethylamine,
(RS)-2-(5-fluoro-indol-1-yl)-1-methyl-ethylamine,
(RS)-2-(6-chloro-5-fluoro-indol-1-yl)-1-methyl-ethylamine,
(R)-2-(5-fluoro-indol-1-yl)-1-methyl-ethylamine,
(S)-2-(6-chloro-5-fluoro-indol-1-yl)-1-methyl-ethylamine,
(R)-2-(6-chloro-5-fluoro-indol-1-yl)-1-methyl-ethylamine,
(RS)-2-(4-methyl-indol-1-yl)-1-methyl-ethylamine,
(RS)-2-(5-bromo-indol-1-yl)-1-methyl-ethylamine,
(RS)-2-(6-fluoro-indol-1-yl)-1-methyl-ethylamine,
(S)-2-(5,6-difluoro-indol-1-yl)-1-methyl-ethylamine,
(R)-2-(5,6-difluoro-indol-1-yl)-1-methyl-ethylamine,
(S)-2-(5-fluoro-4-trifluoromethyl-indol-1-yl)-1-methyl-ethylamine,
(S)-2-(5-fluoro-6-trifluoromethyl-indol-1-yl)-1-methyl-ethylamine,
(S)-2-(4-chloro-5-fluoro-indol-1-yl)-1-methyl-ethylamine, and
(R)-2-(4-chloro-5-fluoro-indol-1-yl)- i-methyl-ethylamine.

6. A pharmaceutical composition comprising an effective amount of a compound of the formula

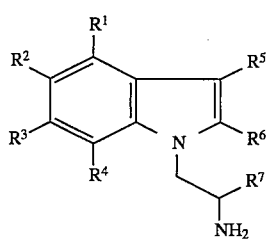

wherein $R^1$ to $R^4$ are, independently, hydrogen, halogen, lower-alkyl, cycloalkyl or trifluoromethyl, $R^5$ and $R^6$ are, independently, hydrogen, halogen, lower-alkyl, cycloalkyl, trifluoromethyl, hydroxy or lower-alkoxy and $R^7$ is lower-alkyl, or a pharmaceutically acceptable acid addition salt thereof and an inert carrier.

7. A method for blocking serotonin receptors in a host requiring such treatment which comprises administering an effective amount of a compound selected from the group consisting of

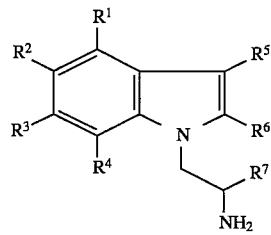

wherein $R^1$ to $R^4$ are, independently, hydrogen, halogen, lower-alkyl, cycloalkyl or trifluoromethyl, $R^5$ and $R^6$ are, independently, hydrogen, halogen, lower-alkyl, cycloalkyl, trifluoromethyl, hydroxy or lower-alkoxy and $R^7$ is lower-alkyl, or a pharmaceutically acceptable acid addition salt thereof.

* * * * *